US008440226B2

(12) United States Patent
Rohloff et al.

(10) Patent No.: US 8,440,226 B2
(45) Date of Patent: May 14, 2013

(54) SOLVENT/POLYMER SOLUTIONS AS SUSPENSION VEHICLES

(75) Inventors: Catherine M. Rohloff, Los Altos, CA (US); Guohua Chen, Sunnyvale, CA (US); Andrew S. Luk, Castro Valley, CA (US); Rupal A. Ayer, Cupertino, CA (US); Paul R. Houston, Hayward, CA (US); Michael A. Desjardin, Sunnyvale, CA (US); Pauline Zamora, Sausalito, CA (US); Stan Lam, Dublin, CA (US)

(73) Assignee: Intarcia Therapeutics, Inc., Hayward, CA (US)

( * ) Notice: Subject to any disclaimer, the term of this patent is extended or adjusted under 35 U.S.C. 154(b) by 0 days.

(21) Appl. No.: 13/526,375

(22) Filed: Jun. 18, 2012

(65) Prior Publication Data

US 2012/0259318 A1 Oct. 11, 2012

Related U.S. Application Data

(63) Continuation of application No. 13/158,137, filed on Jun. 10, 2011, now Pat. No. 8,206,745, which is a continuation of application No. 11/347,562, filed on Feb. 3, 2006, now Pat. No. 8,114,437.

(60) Provisional application No. 60/650,225, filed on Feb. 3, 2005.

(51) Int. Cl.

| | |
|---|---|
| *A61K 9/14* | (2006.01) |
| *A61K 45/00* | (2006.01) |
| *A61K 38/00* | (2006.01) |

(52) U.S. Cl.
USPC .......................... 424/486; 424/85.1; 424/94.5

(58) Field of Classification Search .................. 424/486, 424/85.1, 94.61, 94.5; 514/1.2, 12, 1.5, 12.8
See application file for complete search history.

(56) References Cited

U.S. PATENT DOCUMENTS 3,797,492 A 3/1974 Place
3,987,790 A 10/1976 Eckenhoff et al.

(Continued)

FOREIGN PATENT DOCUMENTS

WO WO 98/27962 7/1998
WO WO 99/33446 A 7/1999

(Continued)

OTHER PUBLICATIONS

Dash, et al., "Therapeutic Applications of Implantable Drug Delivery Systems," Journal of Pharmacological and Toxicological Methods, vol. 40, Issue 1, Jul. 1998, pp. 1-12.

(Continued)

*Primary Examiner* — Blessing Fubara
(74) *Attorney, Agent, or Firm* — Gary R. Fabian; Barbara G. McClung

(57) ABSTRACT

A nonaqueous, single-phase vehicle that is capable of suspending an active agent. The nonaqueous, single-phase vehicle includes at least one solvent and at least one polymer and is formulated to exhibit phase separation upon contact with an aqueous environment. The at least one solvent may be selected from the group consisting of benzyl benzoate, decanol, ethyl hexyl lactate, and mixtures thereof and the at least one polymer may be selected from the group consisting of a polyester, pyrrolidone, ester of an unsaturated alcohol, ether of an unsaturated alcohol, polyoxyethylenepolyoxypropylene block copolymer, and mixtures thereof. In one embodiment, the at least one solvent is benzyl benzoate and the at least one polymer is polyvinylpyrrolidone. A stable, nonaqueous suspension formulation that includes the nonaqueous, single-phase vehicle and an active agent, and a method of forming the same, are also disclosed.

11 Claims, 7 Drawing Sheets

U.S. PATENT DOCUMENTS

| | | | |
|---|---|---|---|
| 4,008,719 | A | 2/1977 | Theeuwes et al. |
| 4,305,927 | A | 12/1981 | Theeuwes et al. |
| 4,865,845 | A | 9/1989 | Eckenhoff et al. |
| 4,874,388 | A | 10/1989 | Wong et al. |
| 5,034,229 | A | 7/1991 | Magruder et al. |
| 5,057,318 | A | 10/1991 | Magruder et al. |
| 5,059,423 | A | 10/1991 | Magruder et al. |
| 5,110,596 | A | 5/1992 | Magruder et al. |
| 5,112,614 | A | 5/1992 | Magruder et al. |
| 5,137,727 | A | 8/1992 | Eckenhoff |
| 5,151,093 | A | 9/1992 | Theeuwes et al. |
| 5,219,572 | A | 6/1993 | Sivaramakrishnan et al. |
| 5,234,692 | A | 8/1993 | Magruder et al. |
| 5,234,693 | A | 8/1993 | Magruder et al. |
| 5,279,608 | A | 1/1994 | Cherif Cheikh |
| 5,308,348 | A | 5/1994 | Balaban et al. |
| 5,312,389 | A | 5/1994 | Theeuwes et al. |
| 5,336,057 | A | 8/1994 | Fukuda et al. |
| 5,368,588 | A | 11/1994 | Bettinger |
| 5,511,355 | A | 4/1996 | Dingler |
| 5,557,318 | A | 9/1996 | Gabriel |
| 5,713,847 | A | 2/1998 | Howard, III et al. |
| 5,728,396 | A | 3/1998 | Peery et al. |
| 5,836,935 | A | 11/1998 | Ashton et al. |
| 5,874,388 | A | 2/1999 | Hsu |
| 5,904,935 | A | 5/1999 | Eckenhoff et al. |
| 5,932,547 | A | 8/1999 | Stevenson et al. |
| 5,972,370 | A | 10/1999 | Eckenhoff et al. |
| 5,976,109 | A | 11/1999 | Heruth |
| 5,985,305 | A | 11/1999 | Peery et al. |
| 5,997,527 | A | 12/1999 | Gumucio et al. |
| 5,997,902 | A | 12/1999 | Maruyama et al. |
| 6,113,938 | A | 9/2000 | Chen et al. |
| 6,124,261 | A | 9/2000 | Stevenson et al. |
| 6,130,200 | A | 10/2000 | Brodbeck et al. |
| 6,132,420 | A | 10/2000 | Dionne et al. |
| 6,156,331 | A | 12/2000 | Peery et al. |
| 6,190,350 | B1 | 2/2001 | Davis et al. |
| 6,217,906 | B1 | 4/2001 | Gumucio et al. |
| 6,235,712 | B1 | 5/2001 | Stevenson et al. |
| 6,248,112 | B1 | 6/2001 | Gambale et al. |
| 6,261,584 | B1 | 7/2001 | Peery et al. |
| 6,270,787 | B1 | 8/2001 | Ayer |
| 6,283,949 | B1 | 9/2001 | Roorda |
| 6,287,295 | B1 | 9/2001 | Chen et al. |
| 6,331,311 | B1 | 12/2001 | Brodbeck et al. |
| 6,375,978 | B1 | 4/2002 | Kleiner et al. |
| 6,395,292 | B2 | 5/2002 | Peery et al. |
| 6,436,091 | B1 | 8/2002 | Harper et al. |
| 6,447,522 | B2 | 9/2002 | Gambale et al. |
| 6,468,961 | B1 | 10/2002 | Brodbeck et al. |
| 6,508,808 | B1 | 1/2003 | Carr et al. |
| 6,524,305 | B1 | 2/2003 | Peterson et al. |
| 6,544,252 | B1 | 4/2003 | Theeuwes et al. |
| 6,670,368 | B1 | 12/2003 | Breault et al. |
| 6,673,767 | B1 | 1/2004 | Brodbeck et al. |
| 6,840,931 | B2 | 1/2005 | Peterson et al. |
| 6,899,887 | B2 | 5/2005 | Ayer |
| 6,939,556 | B2 | 9/2005 | Lautenbach |
| 7,014,636 | B2 | 3/2006 | Gilbert |
| 7,074,423 | B2 | 7/2006 | Fereira et al. |
| 7,163,688 | B2 | 1/2007 | Peery et al. |
| 7,207,982 | B2 | 4/2007 | Dionne et al. |
| 7,241,457 | B2 | 7/2007 | Chen et al. |
| 7,258,869 | B1 | 8/2007 | Berry et al. |
| 7,407,499 | B2 | 8/2008 | Trautman |
| 7,655,254 | B2 * | 2/2010 | Dennis et al. ................. 424/422 |
| 7,682,356 | B2 * | 3/2010 | Alessi et al. ............... 604/892.1 |
| 7,731,947 | B2 | 6/2010 | Eliaz et al. |
| 7,879,028 | B2 * | 2/2011 | Alessi et al. ............... 604/892.1 |
| 8,114,437 | B2 * | 2/2012 | Rohloff et al. ................ 424/486 |
| 8,206,745 | B2 * | 6/2012 | Rohloff et al. ................ 424/486 |
| 2001/0022974 | A1 * | 9/2001 | Ayer ............................. 424/473 |
| 2002/0034532 | A1 | 3/2002 | Brodbeck et al. |
| 2002/0136848 | A1 | 9/2002 | Yoshii et al. |
| 2003/0044467 | A1 | 3/2003 | Brodbeck et al. |
| 2003/0059376 | A1 | 3/2003 | Libbey, III et al. |
| 2003/0060425 | A1 | 3/2003 | Ahlem et al. |
| 2003/0104063 | A1 | 6/2003 | Babcock et al. |
| 2003/0108609 | A1 * | 6/2003 | Berry et al. .................. 424/486 |
| 2003/0180364 | A1 | 9/2003 | Chen et al. |
| 2003/0211974 | A1 | 11/2003 | Brodbeck et al. |
| 2003/0215515 | A1 | 11/2003 | Truong-Le et al. |
| 2004/0001889 | A1 | 1/2004 | Chen et al. |
| 2004/0024069 | A1 | 2/2004 | Chen et al. |
| 2004/0151753 | A1 | 8/2004 | Chen et al. |
| 2004/0224903 | A1 | 11/2004 | Berry et al. |
| 2005/0008661 | A1 | 1/2005 | Fereira et al. |
| 2005/0010196 | A1 | 1/2005 | Fereira et al. |
| 2005/0095284 | A1 | 5/2005 | Trautman |
| 2005/0101943 | A1 | 5/2005 | Ayer et al. |
| 2005/0118206 | A1 | 6/2005 | Luk et al. |
| 2005/0175701 | A1 | 8/2005 | Pan et al. |
| 2005/0266087 | A1 | 12/2005 | Junnarkar et al. |
| 2005/0276856 | A1 | 12/2005 | Fereira et al. |
| 2006/0013879 | A9 | 1/2006 | Brodbeck et al. |
| 2006/0141040 | A1 | 6/2006 | Chen et al. |
| 2006/0142234 | A1 | 6/2006 | Chen et al. |
| 2006/0193918 | A1 | 8/2006 | Rohloff et al. |
| 2006/0216242 | A1 | 9/2006 | Rohloff et al. |
| 2006/0246138 | A1 | 11/2006 | Rohloff et al. |
| 2006/0263433 | A1 | 11/2006 | Ayer et al. |
| 2007/0027105 | A1 | 2/2007 | Junnarkar et al. |
| 2007/0281024 | A1 | 12/2007 | Lautenbach et al. |
| 2008/0112994 | A1 | 5/2008 | Junnarkar et al. |
| 2008/0260840 | A1 | 10/2008 | Alessi et al. |
| 2009/0022727 | A1 | 1/2009 | Houston et al. |
| 2009/0087408 | A1 | 4/2009 | Berry et al. |
| 2009/0202608 | A1 | 8/2009 | Alessi et al. |
| 2010/0092566 | A1 | 4/2010 | Alessi et al. |
| 2011/0104111 | A1 | 5/2011 | Rohloff et al. |
| 2011/0264077 | A1 | 10/2011 | Rohloff et al. |

FOREIGN PATENT DOCUMENTS

| | | | | |
|---|---|---|---|---|
| WO | WO 00/45790 | | | 8/2000 |
| WO | WO 00/54745 | A2 | | 9/2000 |
| WO | WO 01/43528 | A2 | | 12/2000 |
| WO | WO 01/51041 | A | | 7/2001 |
| WO | WO 02/28366 | A2 | | 4/2002 |
| WO | WO 02/43800 | | | 6/2002 |
| WO | WO 02/067895 | A2 | | 9/2002 |
| WO | WO 03/041684 | | * | 5/2003 |
| WO | WO 03/041684 | A2 | | 5/2003 |
| WO | WO 03/041684 | A3 | | 5/2003 |
| WO | WO 03/072113 | | | 9/2003 |
| WO | WO 2004/052336 | | | 6/2004 |
| WO | WO 2004/089335 | A2 | | 10/2004 |
| WO | WO 2005/048930 | A2 | | 6/2005 |

OTHER PUBLICATIONS

International Search Report, dated Aug. 12, 2004 (4 pages).
International Search Report, dated Nov. 4, 2004 (4 pages).
International Search Report, dated Nov. 12, 2004 (4 pages).
PCT International Search Report dated Jul. 28, 2006 (4 pages).

* cited by examiner

SOLVENT/POLYMER SOLUTIONS AS SUSPENSION VEHICLES

CROSS REFERENCE TO RELATED APPLICATION

This application is a continuation of U.S. patent application Ser. No. 13/158,137 filed 10 Jun. 2011 now pending, which is a continuation of U.S. patent application Ser. No. 11/347,562 filed 3 Feb. 2006, now U.S. Pat. No. 8,114,437 which claims the benefit of U.S. Provisional patent application Ser. No. 60/650,225, filed 3 Feb. 2005, now expired, which applications are herein incorporated by reference in their entireties in the present application.

FIELD OF THE INVENTION

The present invention relates to a suspension vehicle capable of uniformly dispersing an active agent and delivering the active agent at a low flow rate. More specifically, the present invention relates to a suspension vehicle that includes a solvent and a polymer and is formulated to exhibit phase separation upon contact with an aqueous environment.

BACKGROUND OF THE INVENTION

There is considerable interest in delivering small molecules or biomolecular substances, such as peptides, polypeptides, proteins, lipoproteins, nucleic acid, hormones, viruses, or antibodies, using implantable drug delivery devices, such as osmotic, mechanical, or electromechanical devices. Implantable drug delivery devices provide improved patient compliance because the devices are not easily tampered with by a patient and are designed to provide therapeutic doses of the biomolecular substance over extended periods of time, such as weeks, months, or even years. Use of the implantable drug delivery device also provides reduced irritation at the site of the implantation compared to daily or multiple injections, fewer occupational hazards for the patients and practitioners, and reduced waste disposal hazards. Implantable drug delivery devices that are capable of delivering a desired dose of a beneficial agent over extended periods of time are known in the art.

However, delivering the biomolecular substance with the implantable drug delivery device is problematic. While the biomolecular substance is active in an aqueous environment, it is only marginally stable in an aqueous environment under ambient conditions. Therefore, a formulation of the biomolecular substance typically requires refrigeration, otherwise it begins to degrade. The biomolecular substance degrades by one or more mechanisms including deamidation, oxidation, hydrolysis, disulfide interchange, or racemization. Significantly, water is a reactant in many of the degradation pathways. In addition, water acts as a plasticizer and facilitates the unfolding and irreversible aggregation of the biomolecular substance. To overcome the stability problems with aqueous formulations of the biomolecular substance, dry powder formulations of the biomolecular substance have been created using known particle formation processes, such as lyophilization, spray-drying, freeze-drying, or dessication of the biomolecular substance. While dry formulations of the biomolecular substances are stable, many delivery methods require flowable forms of the biomolecular substance. For instance, flowable forms are needed for parenteral injections and implantable drug delivery devices.

To form a flowable formulation, a dry, powdered biomolecular substance is typically suspended in a nonaqueous, viscous vehicle. The biomolecular substance must be contained within a formulation that maintains the stability of the biomolecular substance at an elevated temperature (i.e., 37° C. and above) over the operational life of the implantable drug delivery device. The biomolecular substance must also be formulated to allow delivery of the biomolecular substance into a desired environment of operation over an extended period of time. The biomolecular substance must also be formulated to allow delivery at a low flow rate (i.e., less than or equal to approximately 100 μl/day).

U.S. Pat. No. 6,468,961 to Brodbeck, et al., and United States Patent Application Nos. 2004/0024069 and 2004/0151753, both to Chen, et al., disclose a depot composition that includes a viscous gel formed from a polymer and a solvent. The polymer is a polylactide, polyglycolide, caprolactone-based polymer, polycaprolactone, polyanhydride, polyamine, polyurethane, polyesteramide, polyorthoester, polydioxanone, polyacetal, polyketal, polycarbonate, polyorthocarbonate, polyphosphazene, succinate, poly(malic acid), poly(amino acid), polyvinylpyrrolidone (PVP), polyethylene glycol, polyhydroxycellulose, hydroxymethylcellulose, polyphosphoester, polyester, polyoxaester, polybutylene terephthalate, polysaccharide, chitin, chitosan, hyaluronic acid, or copolymer, terpolymer, or mixtures thereof. The solvent includes aromatic alcohols; esters of aromatic acids, such as lower alkyl or aralkyl esters of aryl acids; aromatic ketones, such as aryl, aralkyl, or lower alkyl ketones; and mixtures thereof.

United States Patent Application No. 2003/0108609 to Berry, et al., discloses a stable, nonaqueous single-phase viscous vehicle that includes at least two of a polymer, a solvent, and a surfactant. The vehicle suspends a beneficial agent, which is deliverable at a low flow rate and at body temperature from an implantable drug delivery device. The solvent includes carboxylic acid esters, polyhydric alcohols, polymers of polyhydric alcohols, fatty acids, oils, lauryl alcohol, or esters of polyhydric alcohols. The polymer includes polyesters, pyrrolidones, esters or ethers of unsaturated alcohols, or polyoxyethylenepolyoxypropylene block copolymers. The vehicle is well suited to preparing suspensions that include biomolecular beneficial agents and are stable over extended periods of time, even at elevated temperatures. However, under certain circumstances, a formulation of the vehicle and the beneficial agent may have the potential to inhibit delivery of the beneficial agent into the desired environment of operation. In particular, when the formulation is exposed to an aqueous liquid, such as a physiological fluid, within a delivery conduit of a device used to deliver the formulation, the polymer in the vehicle tends to phase separate from the solvent into the aqueous liquid. As the polymer partitions into the aqueous liquid, the concentration of the polymer within the aqueous liquid may increase to such an extent that a highly viscous polymer gel is formed within the delivery conduit, which results in a partial or complete occlusion of the delivery conduit and interferes with the desired operation of the delivery device. The potential for such occlusions increases where the geometry of the delivery conduit is such that aqueous liquid interfaces with the drug formulation in a confined area over a relatively long period of time (e.g., hours or days).

It would be an improvement in the art to provide a vehicle that facilitates delivery of a formulation of a small molecule or biomolecular substance from a depot composition or an implanted drug delivery device. Ideally, the vehicle is formulated to deliver the therapeutic agent at a controlled rate without blocking or occluding the drug delivery device and/or to maintain the stability of the biomolecular substance over an extended period of time.

BRIEF SUMMARY OF THE INVENTION

The present invention relates to a nonaqueous, single-phase vehicle that is capable of suspending an active agent. The nonaqueous, single-phase vehicle includes at least one solvent and at least one polymer, and is formulated to exhibit phase separation upon contact with an aqueous environment. The at least one solvent may be immiscible with water and the at least one polymer may be soluble in the at least one solvent. The at least one solvent may be selected from the group consisting of benzyl benzoate, decanol, ethyl hexyl lactate, and mixtures thereof. The at least one polymer may be selected from the group consisting of a polyester, pyrrolidone, ester of an unsaturated alcohol, ether of an unsaturated alcohol, polyoxyethylenepolyoxypropylene block copolymer, and mixtures thereof. In one embodiment, the at least one solvent is benzyl benzoate and the at least one polymer is polyvinylpyrrolidone (PVP).

The present invention also relates to a stable, nonaqueous suspension formulation that includes an active agent and a nonaqueous, single-phase vehicle. The nonaqueous, single-phase vehicle includes at least one solvent and at least one polymer and is formulated to exhibit phase separation upon contact with an aqueous environment. The at least one solvent and the at least one polymer may be one of the materials described above. The active agent may be selected from the group consisting of baclofen, glial-cell line-derived neurotrophic factor, a neurotrophic factor, conatonkin G, Ziconotide, clonidine, axokine, an antisense oligonucleotide, adrenocorticotropic hormone, angiotensin I, angiotensin II, atrial natriuretic peptide, B-natriuretic peptide, bombesin, bradykinin, calcitonin, cerebellin, dynorphin N, alpha endorphin, beta endorphin, endothelin, enkephalin, epidermal growth factor, fertirelin, follicular gonadotropin releasing peptide, galanin, glucagon, glucagon-like peptide-1, gonadorelin, gonadotropin, goserelin, growth hormone releasing peptide, histrelin, human growth hormone, insulin, an alpha-, beta-, or omega-interferon, Nesiritide, leuprolide, luteinizing hormone-releasing hormone, motilin, nafarerlin, neurotensin, oxytocin, relaxin, somatostatin, substance P, tumor necrosis factor, triptorelin, vasopressin, growth hormone, nerve growth factor, a blood clotting factor, and a ribozyme. In one embodiment, the at least one solvent is benzyl benzoate, the at least one polymer is polyvinylpyrrolidone, and the active agent is omega-interferon (omega-IFN). The active agent may also be selected from small molecules such as, for example, ocaperidone, risperidone, and paliperidone.

The present invention also relates to a method of preparing a stable, nonaqueous suspension formulation. The method includes providing a nonaqueous, single-phase vehicle that includes at least one polymer and at least one solvent. The nonaqueous, single-phase vehicle exhibits phase separation upon contact with an aqueous environment. An active agent is provided, wherein the active agent is substantially insoluble in the nonaqueous, single-phase vehicle. The active agent and the nonaqueous, single-phase vehicle are mixed to form a stable, nonaqueous suspension formulation. The at least one solvent, the at least one polymer, and the active agent may be one of the materials described above.

BRIEF DESCRIPTION OF THE SEVERAL VIEWS OF THE DRAWINGS

While the specification concludes with claims particularly pointing out and distinctly claiming that which is regarded as the present invention, the advantages of this invention may be more readily ascertained from the following description of the invention when read in conjunction with the accompanying drawings in which:

DETAILED DESCRIPTION OF THE INVENTION

Figure 1:
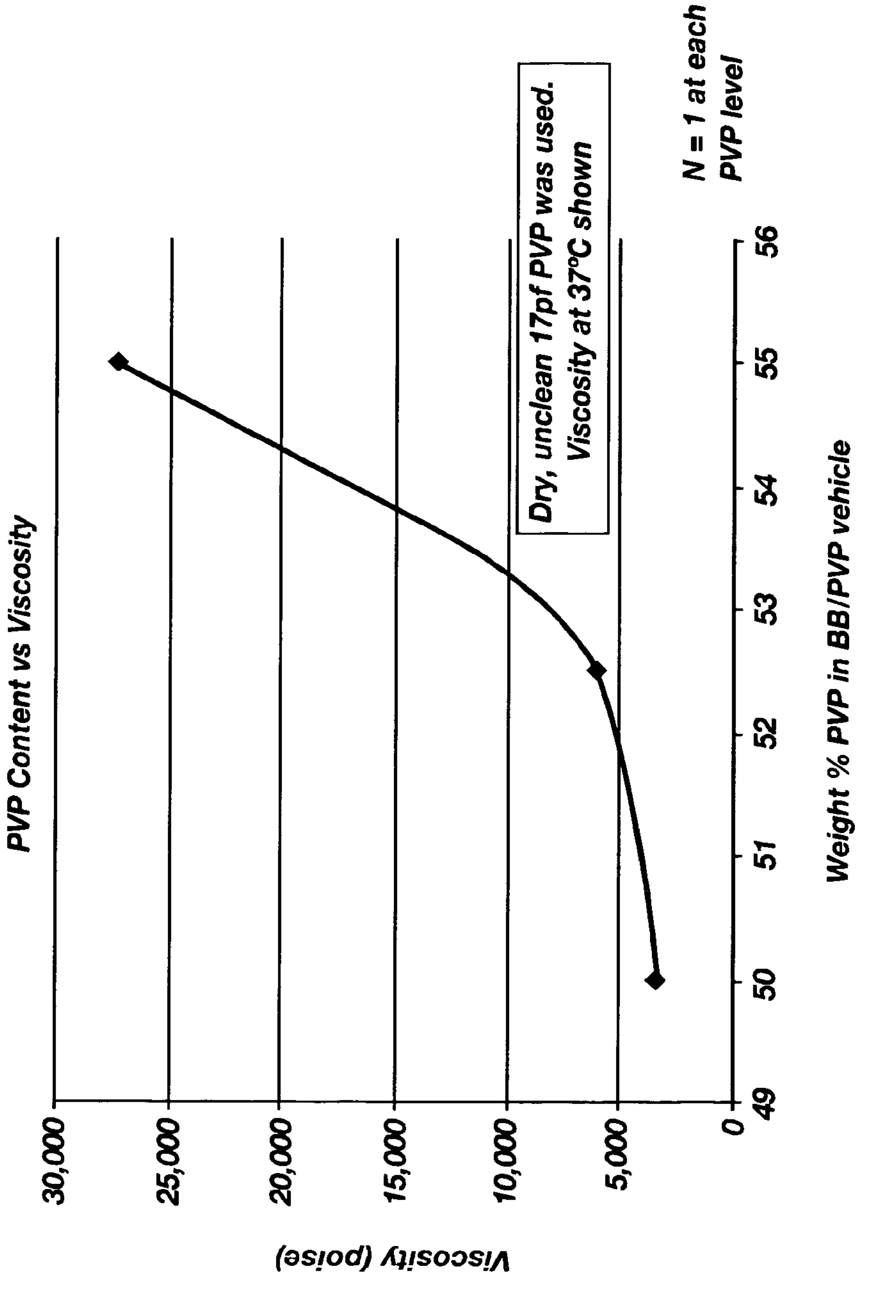
FIG. 1 is a graph illustrating the viscosity of a suspension vehicle that includes benzyl benzoate and PVP as a function of the weight percentage of PVP.

A suspension formulation having a suspension vehicle and an active agent is disclosed. The suspension vehicle is formulated to exhibit phase separation upon contact with an aqueous environment. As used herein, the phrase "phase separation" refers to the formation of multiple phases (e.g., liquid or gel phases) in the suspension vehicle, such as when the suspension vehicle contacts the aqueous environment. In specific embodiments of the invention, the suspension vehicle is formulated to exhibit phase separation upon contact with an aqueous environment having less than approximately 10% water. The suspension vehicle is a single-phase vehicle in which the active agent is dispersed. As used herein, the phrase "single-phase" refers to a solid, semisolid, or liquid homogeneous system that is physically and chemically uniform throughout, as determined by differential scanning calorimetry (DSC). As used herein, the term "dispersed" refers to dissolving, dispersing, suspending, or otherwise distributing the active agent in the suspension vehicle. The suspension vehicle is formulated to provide sustained delivery of the active agent to a patient by delivering the active agent at a low flow rate over an extended period of time. As used herein, the term "patient" refers to a human or another mammal to which the suspension formulation is administered.

The suspension vehicle provides a stable environment in which the active agent is dispersed. The suspension vehicle includes at least one polymer and at least one solvent, forming a solution of sufficient viscosity to uniformly suspend particles of the active agent. The viscosity of the suspension vehicle may prevent the active agent from settling during storage and use of the suspension formulation in, for example, an implantable, drug delivery device. The suspension vehicle is biodegradable in that the suspension vehicle disintegrates or breaks down over a period of time in response to a biological environment. The disintegration of the suspension vehicle may occur by one or more physical or chemical degradative processes, such as by enzymatic action, oxidation, reduction, hydrolysis (e.g., proteolysis), displacement (e.g., ion exchange), or dissolution by solubilization, emulsion or micelle formation. After the suspension vehicle disintegrates, components of the suspension vehicle are absorbed or otherwise dissipated by the body and surrounding tissue of the patient.

The solvent in which the polymer is dissolved may affect characteristics of the suspension formulation, such as the behavior of the active agent during storage and, where applicable, use of the implantable, drug delivery device. The solvent may be selected in combination with the polymer so that the resulting suspension vehicle exhibits phase separation upon contact with the aqueous environment. Optionally, the solvent may be selected in combination with the polymer so that the resulting suspension vehicle exhibits phase separation upon contact with the aqueous environment having less than approximately 10% water. The solvent may be a pharmaceutically acceptable solvent that is not miscible with water. The solvent may also be selected so that the polymer is soluble in the solvent at high concentrations, such as at a polymer concentration of greater than approximately 30%. However, the active agent may be substantially insoluble in the solvent. The solvent may include, but is not limited to, lauryl alcohol, benzyl benzoate, benzyl alcohol, lauryl lactate, CERAPHYL® 31, decanol (also called decyl alcohol), ethyl hexyl lactate, and long chain (C8 to C24) aliphatic alcohols, esters, or mixtures thereof. The solvent used in the suspension vehicle may be "dry," in that it has a low moisture content. In one embodiment, the solvent is benzyl benzoate, which has a solubility in water of less than approximately 0.01%. Using benzyl benzoate as the solvent can be advantageous because benzyl benzoate is used as an excipient in injectable products, such as DELESTROGEN® and FASLODEX®. As such, the risk of the patient suffering adverse reactions to benzyl benzoate is reduced and the cost to demonstrate safety of the benzyl benzoate is decreased.

The polymer may include, but is not limited to, a polyester, pyrrolidone, ester or ether of an unsaturated alcohol, polyoxyethylenepolyoxypropylene block copolymer, or mixtures thereof. The polyester may be polylactic acid or polylacticpolyglycolic acid. The pyrrolidone may be PVP having a molecular weight ranging from approximately 2,000 to approximately 1,000,000. The ester or ether of the unsaturated alcohol may be vinyl acetate. In one embodiment, the polymer is PVP. The polymer used in the suspension vehicle may include one or more different polymers or may include different grades of a single polymer. The polymer used in the suspension vehicle may also be dry or have a low moisture content.

The polymer and the solvent may each be present in the suspension vehicle in an amount sufficient to provide the desired performance of the suspension vehicle. The polymer may be present in the suspension vehicle from approximately 10% to approximately 90% and the solvent may be present from approximately 10% to approximately 90%. The percentages of the polymer and the solvent are provided herein in terms of wt/wt ratios. For instance, the suspension vehicle may include from approximately 25% to approximately 75% of the polymer and from approximately 25% to approximately 75% of the solvent. In one embodiment, the suspension vehicle includes from approximately 40% to approximately 60% of the polymer and from approximately 40% to approximately 60% of the solvent.

The suspension vehicle may exhibit Newtonian behavior. The suspension vehicle is formulated to provide a viscosity that maintains the uniform dispersion of the active agent for a predetermined period of time, which facilitates creation of a suspension formulation that is tailored to provide controlled delivery of the active agent at a desired rate. The viscosity of the suspension vehicle may vary depending on the desired application, the size and type of the active agent, and the loading of the active agent in the suspension vehicle. The viscosity of the suspension vehicle may be varied by altering the type or relative amount of the solvent or polymer used. The suspension vehicle may have a viscosity ranging from approximately 100 poise to approximately 1,000,000 poise, such as from approximately 1,000 poise to approximately 100,000 poise. The viscosity is measured at 37° C., at a shear rate of $10^{-4}$/sec, using a parallel plate rheometer. In one embodiment, the viscosity of the suspension vehicle ranges from approximately 5,000 poise to approximately 50,000 poise. While the suspension vehicle exhibits phase separation when contacted with the aqueous environment, the suspension vehicle may exhibit substantially no phase separation as a function of temperature. For instance, at a temperature ranging from approximately 0° C. to approximately 70° C. and upon temperature cycling, such as cycling from 4° C. to 37° C. to 4° C., the suspension vehicle may exhibit no phase separation. In particular embodiments of the invention, the suspension vehicle exhibits phase separation when contacted with the aqueous environment having less than approximately 10% water.

The suspension vehicle may be prepared by combining the polymer and the solvent under dry conditions, such as in a drybox. The polymer and solvent may be combined at an elevated temperature, such as from approximately 40° C. to approximately 70° C., and allowed to liquefy and form the single phase. The ingredients may be blended under vacuum to remove air bubbles produced from the dry ingredients. The ingredients may be combined using a conventional mixer, such as a dual helix blade or similar mixer, set at a speed of approximately 40 rpm. However, higher speeds may also be used to mix the ingredients. Once a liquid solution of the ingredients is achieved, the suspension vehicle may be cooled to room temperature. DSC may be used to verify that the suspension vehicle is a single phase.

The active agent may be added to the suspension vehicle to form the suspension formulation. The active agent may be a biomolecular substance that has biological activity or is capable of being used to treat a disease or other pathological condition. The active agent may include, but is not limited to, a peptide, polypeptide, protein, amino acids, nucleotides, a polymer of an amino acid residue(s) or a nucleotide residue(s), hormone, virus, antibody, or mixtures thereof. The biomolecular substance may also be a conjugated protein, such as a lipoprotein or post translationally modified form thereof, such as a glycosylated protein or a protein substance having D-amino acids, modified, derivatized, or non-naturally occurring amino acids in the D- or L-configuration, and/or peptomimetic units. The biomolecular substance may be naturally derived, synthetically produced, or recombinantly produced. The active agent may also be an organic compound, such as a drug, medicine, vitamin, nutrient, or food supplement. The active agent may be used in a solid state, such as a powder, crystalline, or amorphous state. As such, the active agent may be dry or may have a low moisture content. The active agent may be stable at ambient and physiological temperatures in the solid state. The active agent may also be used in the form of a pharmaceutically acceptable salt, such as a salt of an inorganic acid, an organic acid, an inorganic base, or an organic base. As previously mentioned, the active agent may have little or no solubility in the suspension vehicle. The active agent can be selected to provide a therapeutic or beneficial effect when administered to the patient. For the sake of example only, the active agent may be used as a treatment for Hepatitis C, heart disease, diabetes, cancer, bone disease, autoimmune disease, gastrointestinal diseases, respiratory disease, kidney disease, liver disease, circulatory diseases, blood disorders, hormonal disorders, genetic disorders, metabolic disorders, thyroid disease, or central nervous system disorders.

Examples of active agents that may be utilized in the suspension formulation include, but are not limited to, baclofen, glial-cell line-derived neurotrophic factor (GDNF), neurotrophic factors, conatonkin G, Ziconotide, clonidine, axokine, antisense oligonucleotides, adrenocorticotropic hormone, angiotensin I and II, atrial natriuretic peptide, B-natriuretic peptide (BNP), bombesin, bradykinin, calcitonin, cerebellin, dynorphin N, alpha and beta endorphin, endothelin, enkephalin, epidermal growth factor, fertirelin, follicular gonadotropin releasing peptide, galanin, glucagon, glucagon-like peptide (GLP)-1, gonadorelin, gonadotropin, goserelin, growth hormone releasing peptide, histrelin, human growth hormone, insulin, interferons (IFN), such as omega-IFN, leuprolide, Nesiritide, luteinizing hormone-releasing hormone (LHRH), motilin, nafarerlin, neurotensin, oxytocin, relaxin, somatostatin, substance P, tumor necrosis factor, triptorelin, vasopressin, growth hormone, nerve growth factor, blood clotting factors, and ribozymes. The active agent may also be selected from small molecules such as, for example, ocaperidone, risperidone, and paliperidone. Analogs, derivatives, antagonists, agonists, and pharmaceutically acceptable salts of the active agents mentioned above may also be used. In one embodiment, the active agent is omega-IFN.

The amount of the active agent present in the suspension formulation may vary depending on the potency of the active agent, the disease or condition to be treated, the solubility of the active agent, the dose to be administered, the duration of administration, and the desired release rate. The active agent may be present in the suspension formulation in an amount that ranges from approximately 0.1% (w/w) to approximately 50% (w/w). The suspension formulation may include from approximately 50% (w/w) to 99.9% (w/w) of the suspension vehicle. In one embodiment, the particle containing the active agent is present in the suspension formulation at approximately 3-12% 10% (w/w).

The active agent used in the suspension formulation may be provided as a stabilized, dry powder that is produced by spray-drying, freeze-drying, a supercritical fluid process, dessication, granulation, grinding, milling, precipitation, homogenization, or a coating process, as known in the art. To provide the active agent as the dry powder, the active agent may be formulated with one or more adjuvants, excipients, stabilizers, bulking agents, preservatives, or coating agents, as known in the art. For instance, the active agent may be formulated with at least one of citrate, histidine, succinate, methionine, sucrose, and dextran. In one embodiment, the suspension formulation includes omega-IFN:sucrose:methionine:citrate at a ratio of 1:2:1:2.15.

The suspension formulation may be used in the implantable, drug delivery device to provide sustained delivery of the active agent over an extended period of time, such as over weeks, months, or up to approximately one year. The suspension formulation may be prepared by dispersing the active agent in the suspension vehicle. The suspension vehicle may be heated and the active agent added to the suspension vehicle under dry conditions. The ingredients may be mixed under vacuum at an elevated temperature, such as from approximately 40° C. to approximately 70° C. The ingredients may be mixed at a sufficient speed, such as from approximately 40 rpm to approximately 120 rpm, and for a sufficient amount of time, such as approximately 15 minutes, to achieve a uniform dispersion of the active agent in the suspension vehicle. The mixer may be a dual helix blade or other suitable mixer. The resulting mixture may be removed from the mixer, sealed in a dry container to prevent water from contaminating the suspension formulation, and allowed to cool to room temperature before loading into the implantable, drug delivery device. The suspension formulation may be loaded into the implantable, drug delivery device by conventional techniques. The resulting suspension formulation may be stable when stored at elevated temperatures or for an extended period of time.

The suspension formulation may also be used in the form of depot injections to provide sustained delivery of biologically active macromolecules and small molecule compounds. The suspension formulation may be designed to deliver agents for periods of days to months. Alternatively, the suspension formulation may be loaded into an implantable, drug delivery device, which may be capable of delivering the active agent at a desired flow rate over a desired period of time. For example, the suspension formulation may be delivered by an osmotically, mechanically, electromechanically, or chemically driven drug delivery devices. The flow rate at which the active agent is delivered may be less than approximately 100 μl/day, such as from approximately 0.5 μl/day to approximately 5 μl/day. The active agent may be delivered over a period ranging from more than approximately one week to approximately one year or more. The implantable, drug delivery device may include a reservoir having at least one orifice through which the active agent is delivered. The suspension formulation may be stored within the reservoir. The suspension formulation may also be delivered from a drug delivery device that is not implantable or implanted. In one embodiment, the implantable, drug delivery device is osmotically driven, such as a DUROS® implant, which is available from ALZA Corp. (Mountain View, Calif.). The DUROS® implant may enable continuous delivery of the active agent for an extended duration, such as for up to approximately one year.

Other exemplary implantable, drug delivery devices may include regulator-type implantable pumps that provide constant flow, adjustable flow, or programmable flow of the active agent, such as those available from Codman & Shurtleff, Inc. (Raynham, Mass.), Medtronic, Inc. (Minneapolis, Minn.), and Tricumed Medinzintechnik GmbH (Germany).

Phase separation of the suspension vehicle may occur when the suspension vehicle contacts the aqueous environment, forming a second phase that is rich in water and the polymer. The second phase includes substantially no solvent. Since the active agent is stable in nonaqueous and dilute aqueous environments, the active agent may remain stably dispersed after the phase separation occurs. In contrast, the active agent is not stable in environments that include moderate quantities of water, such as from approximately 10% to 25% water.

In a particular embodiment where a drug delivery device is implanted in the patient, water from surrounding tissues may enter one end of the implantable, drug delivery device through a semipermeable membrane. The water may also cause an osmotic engine in the implantable, drug delivery device to swell, displacing a piston and releasing the suspension formulation from a second end of the implantable, drug delivery device and into the patient's body.

Without being bound to any theory, it is believed that the suspension vehicle is capable of effectively delivering the active agent to the patient due to the environment that the active agent encounters as the active agent transitions from the dry suspension formulation to the dilute aqueous environment. If the suspension vehicle is incorporated into an implantable, drug delivery device, the suspension vehicle is capable of effectively delivering the active agent to the patient due to the environment that the active agent encounters as the active agent transitions from the dry suspension formulation within the implantable, drug delivery device to the dilute aqueous environment outside of the implantable drug delivery device.

The following examples serve to explain embodiments of the present invention in more detail. These examples are not to be construed as being exhaustive or exclusive as to the scope of this invention.

EXAMPLES

Example 1

Stability and In Vitro Release of Omega-IFN in a Benzyl Benzoate and a Benzyl Benzoate/Benzyl Alcohol Suspension Vehicle The stability of omega-IFN for three months at 40° C. in two suspension vehicles was determined. One of the suspension vehicles included PVP dissolved in benzyl benzoate. The second suspension vehicle included PVP dissolved in a 90/10 benzyl benzoate/benzyl alcohol mixture. A release rate study at 37° C. was also performed. The materials used in the stability and release rate studies are shown in Table 1.

TABLE 1

| Materials To Be Used in the Stability and Release Rate Studies |
|---|
| Spray-dried omega-IFN: sucrose:methionine:citrate (1:2:1) in 25 mM citrate buffer |
| Benzyl benzoate (BB) |
| Benzyl alcohol (BA) |
| Polyvinylpyrrolidone (PVP) |
| Citrate Buffer |
| Phosphate Buffered Saline (PBS) |
| Piston, fluoroelastomer |
| DUROS ® Osmotic Tablet |
| Tecophilic HP-60D-33 Membrane (g2) Blue NB 7443:155 |
| Titanium Reservoir (g2) |
| Polyethylene Glycol 400 |
| Silicone Fluid, MDM 350 |

TABLE 1-continued

| Materials To Be Used in the Stability and Release Rate Studies |
|---|
| Spiral Diffusion Moderator (DM), high density polyethylene (HDPE), 10 mil, 0.43 mm |
| 10 cc OSGE Glass Syringes |

To produce the spray-dried omega-IFN, omega-IFN was combined with sucrose and methionine dissolved in a 25 mM pH 6.0 citrate buffer and then spray-dried. Spray-drying was conducted and particles collected in a clean, dry air isolator. Particles were tested for purity, protein content, moisture content, oxidation, deamidation, degradation, aggregation, and particle size distribution, as known in the art.

Since the solvents are likely to contain peroxide residues, the peroxides were removed from the benzyl benzoate and benzyl alcohol before preparing the suspension vehicle. To remove the peroxides, alumina was mixed with each of the benzyl benzoate and benzyl alcohol for 30 minutes. The solvents were then filtered through a 0.2 μm filter and stored in a sealed vial under nitrogen. The peroxide levels were measured for each of the benzyl benzoate and benzyl alcohol, as known in the art, before using the solvents in the suspension vehicle. Before use, the PVP was treated with a solution of methionine to reduce the peroxide content. The solution was then diafiltered to remove the methionine, and lyophilized to remove water, leaving a cake of the PVP. Peroxide levels in the PVP were measured as known in the art.

The suspension vehicle was prepared in a DIT mixer at 65° C. The water bath temperature was set to approximately 65° C. and the mixer was preheated. Appropriate amounts of the benzyl benzoate and/or benzyl alcohol were weighed into the mixing bowl. An appropriate amount of the PVP was weighed and transferred into the mixing bowl. The mixing bowl was mounted and the ingredients stirred to incorporate the PVP into the solvent. A vacuum (−5 to −10 in Hg) was applied during the mixing. After the PVP was visually incorporated into the solvent, the vacuum was increased to −30 in Hg, the bowl temperature adjusted to 60° C., and the ingredients were mixed for two hours. The suspension vehicle was discharged into a glass jar and degassed in a vacuum oven set at 60° C. and −30 in Hg for approximately 4-6 hours. The solvent/PVP ratio was selected so that the suspension vehicle had a viscosity of between 10,000 poise and 20,000 poise. As shown in FIG. 1, the viscosity of the BB/PVP suspension vehicle is within the desired range.

The suspension formulation including the suspension vehicle and the omega-IFN particles was prepared in a drybox under nitrogen. A hot plate was moved into the drybox and preheated to 60° C. Appropriate amounts of the omega-IFN and the suspension vehicle were weighed into a glass beaker. Using a stainless steel spatula, the omega-IFN particles were manually incorporated into the suspension vehicle while warming the suspension vehicle with the hotplate. The suspension formulation was mixed by hand for 15 minutes. The suspension formulation included 1:2:1 omega-IFN:sucrose: methionine by weight with 25 mM citrate buffer. The particle loading of omega-IFN in the suspension was approximately 10%, which is equivalent to a drug loading of approximately 1.7%. This is consistent with a unit dose of 25 μg/day of the omega-IFN.

Using a spatula, the suspension formulation was filled into a 10 mL OSGE syringe and the syringe plunger inserted to seal the syringe. An oven was preheated to 60° C. and the filled syringe was transferred to the vacuum oven while a nitrogen flow was on to purge the vacuum oven of oxygen. The plunger was removed and a deaeration spring inserted into the syringe. The formulation was allowed to equilibrate to oven temperature. The spring was rotated at a target of 100 rpm and a vacuum slowly applied until approximately −30 in Hg was attained. The spring was used to mix the suspension formulation for 30 minutes under vacuum. After deaeration, the plunger was inserted into the syringe and excess air was removed. The syringe was sealed in polyfoil and stored refrigerated (at 2° C.-8° C.).

System samples for the release rate and stability studies were filled on the benchtop under ambient conditions. To form the systems, subassemblies were produced by lubricating the reservoirs and pistons with SMF 350. The piston was inserted into the reservoir and ~20 μL of PEG400 was dispensed on the piston. Two osmotic tablets were inserted into the subassembly and an annealed and dried membrane was inserted into the reservoir. The subassemblies were annealed for 30 minutes at 65° C. A filling needle was attached to the syringe containing the suspension formulation. The glass syringe was loaded into a Harvard syringe pump with a heating block surrounding the barrel of the syringe and heated to 65° C. The subassembly was placed on the needle and the implant reservoir filled to within approximately ¼" of the end. Aliquots of the suspension formulation for stability testing were dispensed into glass vials. The vials were flushed with nitrogen, capped, sealed, and stored at 40° C.

To test the systems, the membrane end was placed into a stoppered VACUTAINER® with 3 mL of PBS (phosphate buffer) and the capillary or diffusion moderator end of the assembly was placed into a dry vial (primed) or a vial filled with 3 mL of citrate buffer (unprimed). The system was placed into a 37° C. oven or water bath. For primed systems, the diffusion moderator side vial was filled with citrate buffer after the suspension formulation was observed to exit from the implants (several days to 1 week). For the primed systems, the buffer vial was replaced with a new vial containing fresh buffer one day after filling the diffusion moderator side vial. The old vial was submitted for protein assay. Once per week, the vial was removed from the diffusion moderator of the system for protein assay determination. A new vial with buffer was placed onto the system and the implant returned to 37° C. The samples for protein assay were stored in a refrigerator at 4° C.

Figure 2:
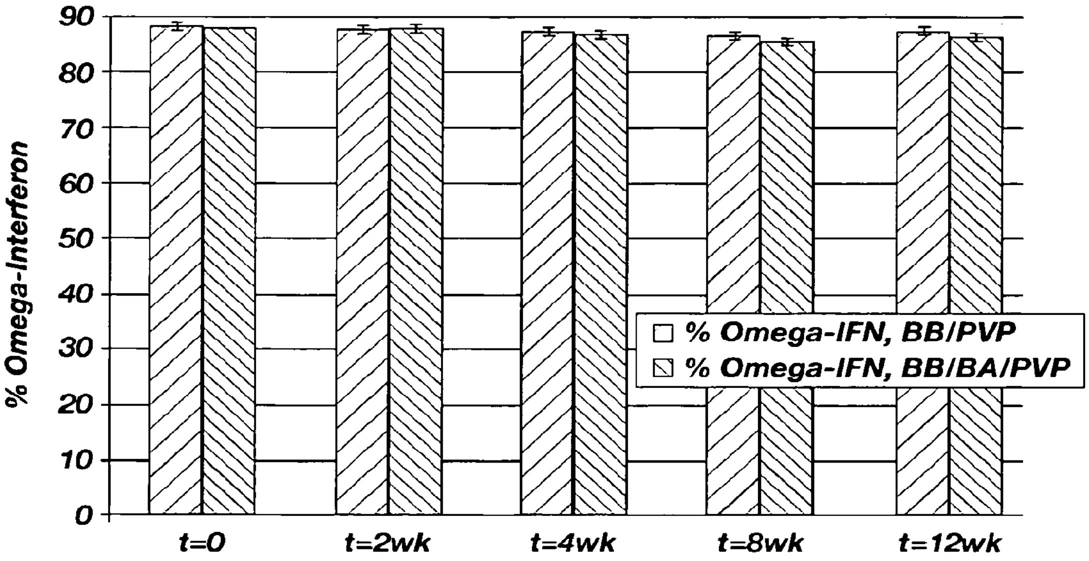
FIG. 2 illustrates the percentage of total omega-IFN that appears as the unaltered omega-IFN main peak in suspension vehicles that include (i) benzyl benzoate and PVP and (ii) benzyl benzoate, benzyl alcohol, an d PVP at 40° C. as a function of time.
Figure 3:
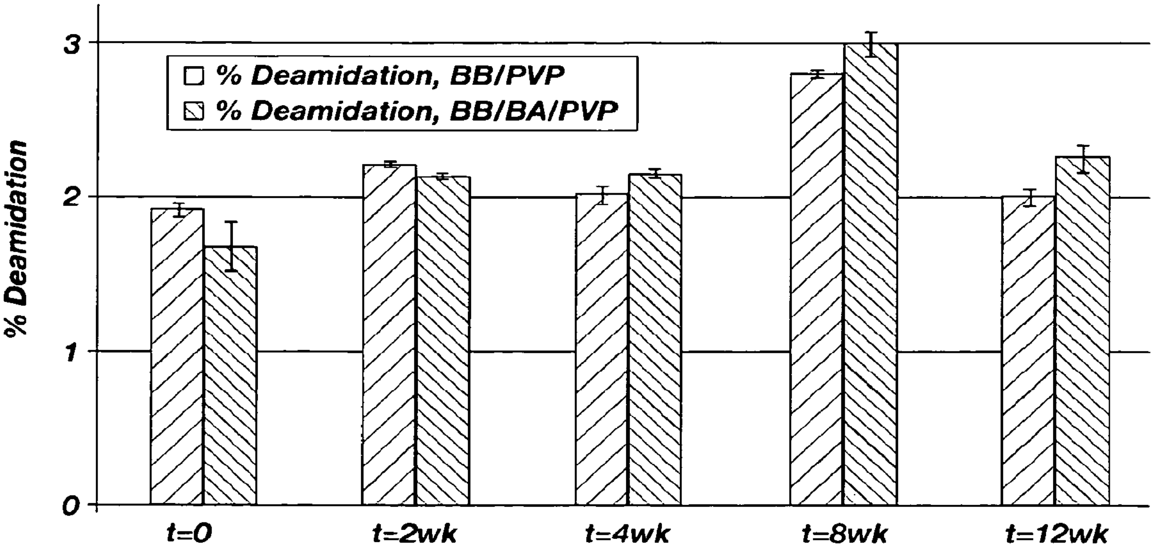
FIG. 3 illustrates the percentage of the total omega-IFN present in the suspension vehicle that is in the deamidated state in suspension vehicles that include (i) benzyl benzoate and PVP and (ii) benzyl benzoate, benzyl alcohol, and PVP at 40° C. as a function of time.
Figure 4:
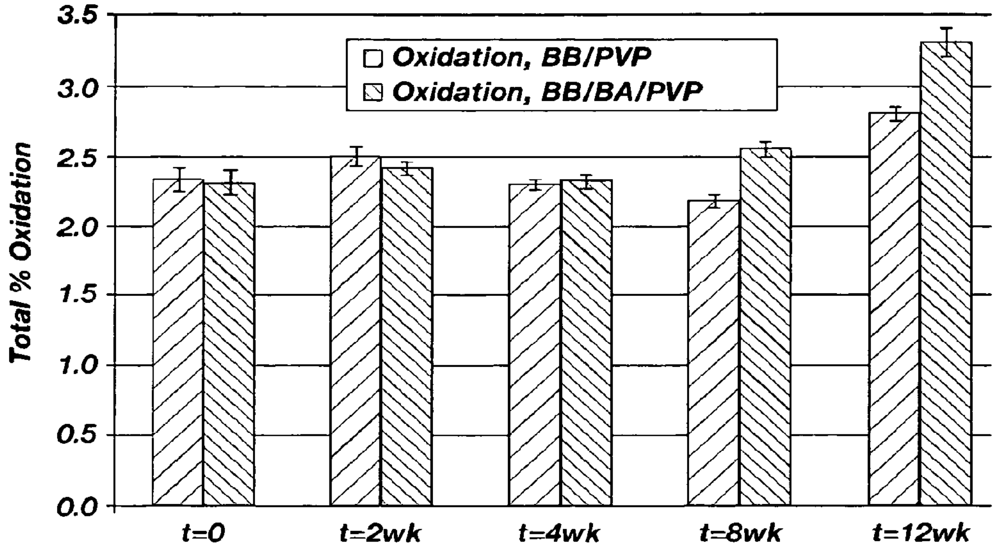
FIG. 4 illustrates the total percentage of the total omega-IFN present in the suspension vehicle that is in the oxidated state in suspension vehicles that include (i) benzyl-time.
Figure 5:
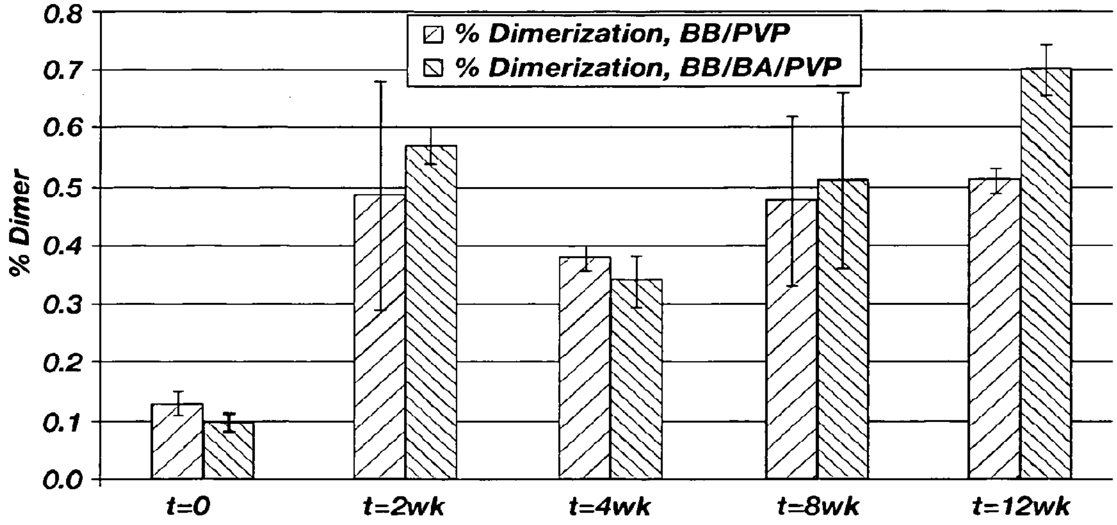
FIG. 5 illustrates the percentage of dimerization of omega-IFN in suspension vehicles that include (i) benzyl benzoate and PVP and (ii) benzyl benzoate, benzyl alcohol, and PVP at 40° C. as a function of time.

The stability of the omega-IFN in the suspension formulation was measured after storage at 40° C. in glass vials flushed with nitrogen. The stability samples were tested in triplicate at t=0, 2, 4, 8, and 12 weeks. The samples were analyzed using reversed-phase high pressure liquid chromatography (RP-HPLC) to determine purity with respect to oxidation and deamidation, and using size exclusion chromatography (SEC) to determine purity with respect to aggregation and precipitation. As shown in FIG. 2, the measured levels of omega-IFN did not change over time in the benzyl benzoate/PVP suspension vehicle. In addition, as shown in FIG. 3, deamidation of the omega-IFN was unchanged between 0 and 12 weeks. Oxidation of the omega-IFN was also unchanged between 0 and 8 weeks but increased slightly after 12 weeks, as shown in FIG. 4. Dimerization levels of the omega-IFN increased from 0 to 2 weeks but did not increase from 2 to 12 weeks, as shown in FIG. 5.

A rate at which the suspension vehicles released the omega-IFN into an aqueous medium at 37° C. was determined. The release rate study was performed using the systems described above. The spiral diffusion moderator was formed from HDPE having an internal diameter of 0.43 mm and a path length of 5 cm. The groups and group size in the release rate study are shown in Table 2.

TABLE 2

Release Rate Experimental Plan

| Start-up Conditions | Suspension 191-1 BB/PVP |
|---|---|
| Dry start, spiral DM | 12 |
| Wet start, spiral DM | 12 |

The citrate buffer included 50 mM citric acid at pH 2 with 0.2% sodium azide added as an antibacterial agent. In all systems, the membrane side of the system is exposed to PBS.

Figure 6:
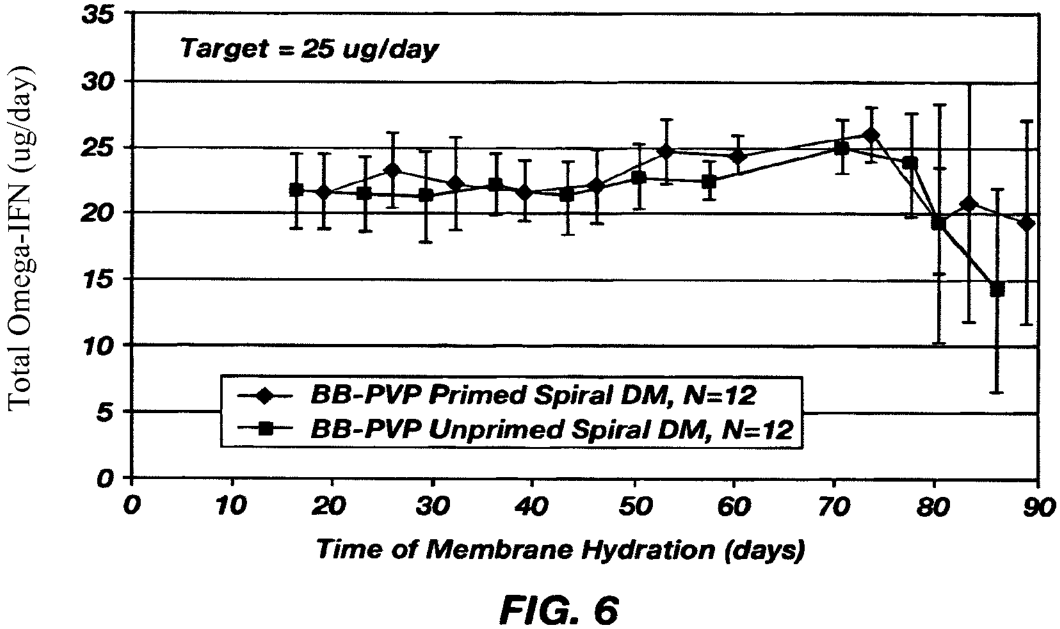
FIGS. 6 and 7 illustrate the average total omega-IFN released and the average percentage of soluble omega-IFN released, respectively, from a suspension vehicle that includes benzyl benzoate and PVP.
Figure 7:
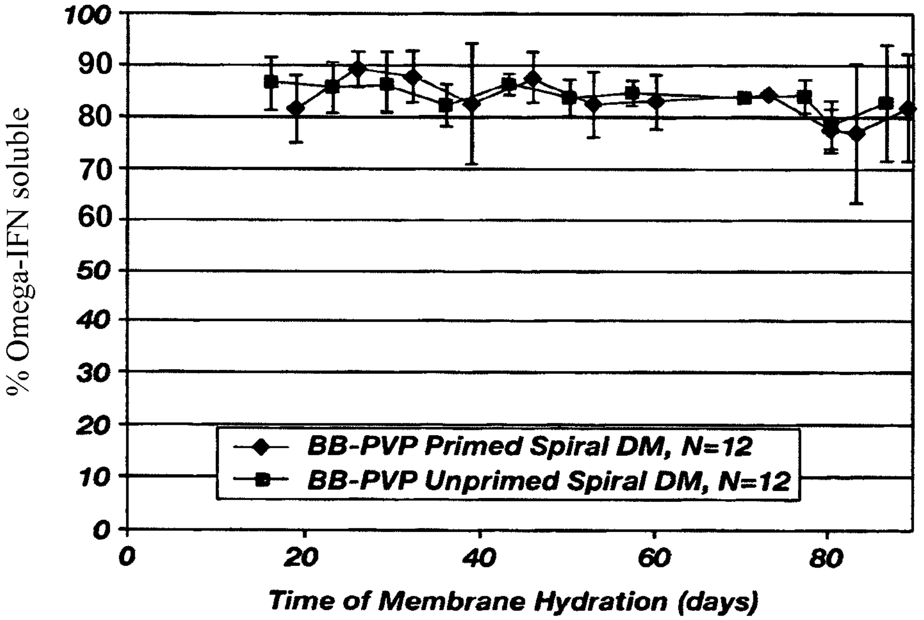

As shown in FIGS. 6 and 7, good in vitro release performance was observed with the benzyl benzoate/PVP suspension vehicle when the suspension vehicle contacted citrate buffer at 37° C. In addition, at day 89, all of the systems had intact membranes. The average total omega-IFN released was also near the target (25 μg/day) through 70 days.

Example 2

In Vivo and In Vitro Testing of Suspension Formulations Using a Straight Diffusion Moderator Four suspension formulations were tested under in vivo conditions over 90 days in rats to determine stability and in vivo release of the omega-IFN. The suspension formulations included omega-IFN as the active agent, PVP or dioleoylphosphocholine (DOPC) as the thickening agent, and lauryl alcohol (LA), benzyl benzoate, benzyl alcohol, or Vitamin E as the solvent. This experiment was designed to concentrate on the suspension formulations and used a straight polyetheretherketone (PEEK) diffusion moderator having a 0.25 mm diameter and a 15 mm length to minimize water ingress. During the experiment, efforts were made to minimize the moisture levels to which the suspension formulation was exposed. The suspension formulations were tested to determine omega-IFN release in vivo from the DUROS® systems at t=5, 9, and 13 days; failure rates (system integrity) of in vivo systems at 45 days (n=3) and 90 days (n=20) after implantation; stability assessment at 5° C. for 3, 6, and 12 months and 40° C. for 1, 2, 3, and 6 months; and in vitro release rate pumping into the air. The materials used in this experiment are shown in Table 3.

TABLE 3

Materials Used in the Studies

| Material |
|---|
| Omega-IFN |
| Sucrose |
| Methionine |
| Citrate buffer |
| Povidone 17PF (cleaned) |
| Lauryl Alcohol |
| Benzyl Benzoate |
| Benzyl Alcohol |
| DOPC |
| Vitamin E |

TABLE 3-continued

| Materials Used in the Studies |
|---|
| DUROS ® Implants |
| C-FLEX ® Piston |
| Fluoroelastomer Piston |
| DUROS ® Osmotic Tablet |
| Tecophilic HP-60D-33 |
| DUROS ® Membrane |
| Titanium Reservoir (Gen 3) with colored band |
| Polyethylene Glycol 400 |
| Silicone Fluid, MDM 350 |
| Straight PEEK DM (0.25 × 15 mm) |

The DUROS® implants used a 150 microliter Gen 3 titanium reservoir with a colored band (drawing no. 28503) fitted with clear Tecophilic HP-60D-33 membranes annealed for 7 days at 65° C.

Each of the suspension vehicles was prepared in a 60 g lot. To minimize residual moisture levels, lyophilized PVP (Povidone) was used. The moisture content of the PVP was measured before preparing the suspension vehicles. The PVP-based suspension vehicles were prepared using a Lightnin Overhead Mixer fitted with a spatula blade for the stirring paddle. The DOPC-based vehicle was prepared on a Keynes mixer. The suspension vehicles were visually inspected for particulates before proceeding. The suspension vehicles were also inspected for phase separation under the microscope at 40° C., 5° C., 0° C., and −5° C. A summary of the compositions of the suspension vehicles is presented in Table 4.

The omega-IFN was prepared as described in Example 1, except that the final target composition of the omega-IFN particles was 1:2:1:2.15 (omega-IFN:sucrose:methionine:citrate). Each suspension formulation had a target particle loading of approximately 10% (w/w). The incorporation of the omega-IFN particles into the suspension vehicle was conducted in a Scott Turbon Mixer in 25 g lots. Following deaeration, the samples were filled in 10 mL syringes and sealed in polyethylene and polyfoil pouches. Samples of the suspension formulations were stored refrigerated until filling.

TABLE 4

Target Compositions of Suspension Formulations

| | Suspension Vehicle Composition | | | | Drug Particle Composition | | | |
|---|---|---|---|---|---|---|---|---|
| Formulation | Solvent | Content (% w/w) | Agent | Content (% w/w) | Sucrose (% w/w) | Methionine (% w/w) | Citrate (% w/w) | ω-INF (% w/w) |
| PDP7-200-1 | LA | 40.5 | PVP | 49.5 | 3.3% | 1.6% | 3.5% | 1.6% |
| PDP7-200-2 | BB | 44.1 | PVP | 45.9 | 3.3% | 1.6% | 3.5% | 1.6% |
| PDP7-200-3 | BA | 35.1 | PVP | 54.9 | 3.3% | 1.6% | 3.5% | 1.6% |
| PDP7-200-4 | Vit. E | 43.2 | DOPC | 46.8 | 3.3% | 1.6% | 3.5% | 1.6% |

The subassemblies were prepared as described in Example 1. The subassemblies and diffusion moderators for the systems were sterilized by gamma irradiation. The subassemblies were passed into and out of the drybox without subjecting the systems to purging to avoid the implants experiencing a reduced pressure environment. The subassemblies were filled with the suspension formulation in the drybox using a heated syringe pump. The systems were then placed into labeled vials with their membrane side down and stoppered, but not crimped. The systems were removed from the drybox and fitted with a straight PEEK diffusion moderator with channel dimensions of 0.25 mm×15 mm. The vials were opened just prior to diffusion moderator insertion. The vials were then restoppered and brought back into the drybox in batches to ensure that the exposure time outside the drybox did not exceed 30 minutes. Each system was equilibrated unstoppered in the drybox for 30 minutes before being restoppered and crimped. The vials were then taken out of the drybox and the air bubbles in each system were assessed using X-rays. Ten systems and diffusion moderators were weighed pre- and post-filling, as well as three systems filled with silicone medical fluid. This data was used to assess the amount of air in each system. Systems were built for in vivo studies and stability. Three systems were exposed to the ambient environment for 30 minutes to quantify moisture uptake.

Each of the systems was characterized as indicated in Table 5. The homogeneity of each of the system samples was tested by monitoring the content of the omega-IFN at the beginning, middle, and end of the batch in replicates of three. This data was also used as the t=0 stability data point.

TABLE 5

Characterization Testing of Systems

| Tests | Sampling quantity and format per suspension formulation |
|---|---|
| In Vivo | 29 Implants |
| Protein Content Assay (homogeneity + stability) | 3 × 0.2 g (beginning) in vials (t = 0 homogeneity) |
| Protein Content Assay (homogeneity + stability) | 3 × 0.2 g (middle) in vials (t = 0 homogeneity) |
| Protein Content Assay (homogeneity + stability) | 3 × 0.2 g (end) in vials (t = 0 homogeneity) |
| Protein Content Assay (homogeneity + stability) | 21 Implants (stability n = 3, 7 conditions) |
| Bioburden | 3 Implants |
| Endotoxin | 1 Implant |
| X-ray | All |
| Viscosity | 1 ml |
| Density | 10 systems (these systems can be also used for stability) |
| Moisture (30 min exposure) | 3 systems (no DM insertion required. Fill from beginning of the syringe.) |

TABLE 5-continued

Characterization Testing of Systems

| Tests | Sampling quantity and format per suspension formulation |
|---|---|
| Moisture of batch | 0.3 g (vial) t = 0 |
| Moisture (stability) | Extra in vivo implants over 25 will be used for moisture stability studies. |

A more detailed summary of the stability sampling is provided in Table 6.

TABLE 6

Summary of Stability Samples

| | Sample Number of Samples Sample | | | | | | |
|---|---|---|---|---|---|---|---|
| | 5° C. (Temperature) | | | 40° C. (Temperature) Sample | | | |
| Particles | Time point (months) 3 0.05 g | Time point (months) 6 0.05 g | Time point (months) 12 0.05 g | Time point (months) 1 0.05 g | Time point (months) 2 0.05 g | Time point (months) 3 0.05 g | Time point (months) 6 0.05 g |
| 1 | 3 sys. | 3 sys. | 3 sys. | 3 sys. | 3 sys. | 3 sys. | 3 sys. |
| 2 | 3 sys. | 3 sys. | 3 sys. | 3 sys. | 3 sys. | 3 sys. | 3 sys. |
| 3 | 3 sys. | 3 sys. | 3 sys. | 3 sys. | 3 sys. | 3 sys. | 3 sys. |
| 4 | 3 sys. | 3 sys. | 3 sys. | 3 sys. | 3 sys. | 3 sys. | 3 sys. |

Figure 8:
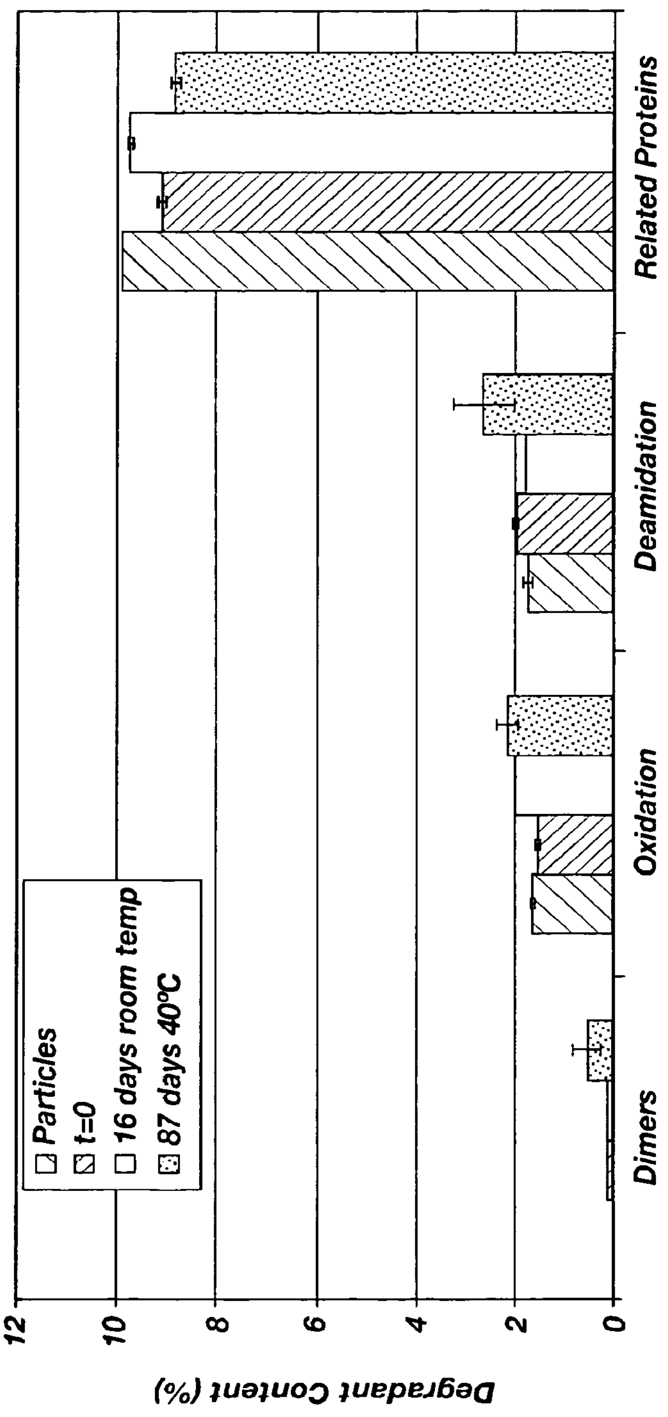
FIG. 8 illustrates the stability (dimerization, oxidation, deamidation, and related proteins) of omega-IFN in a suspension vehicle that includes benzyl benzoate and PVP.

These additional systems were sampled for stability testing of omega-IFN in suspension across all formulations. Stability test systems were sealed in glass vials under nitrogen. Stability testing for omega-IFN in each suspension formulation was performed at 1, 2, 3, and 6 months at 40° C. and at 3, 6, and 12 months at 5° C. As a control, samples of omega-IFN particles were sealed in glass vials under nitrogen and assayed at 1, 2, 3 and 6 months at 40° C. and at 3, 6, and 12 months at 5° C. Three stability samples were assayed for each time/temperature. Extra samples were packaged and incorporated in the stability plan as moisture studies. The stability of omega-IFN in the suspension vehicle that includes benzyl benzoate and PVP is shown in FIG. 8.

Figure 9:
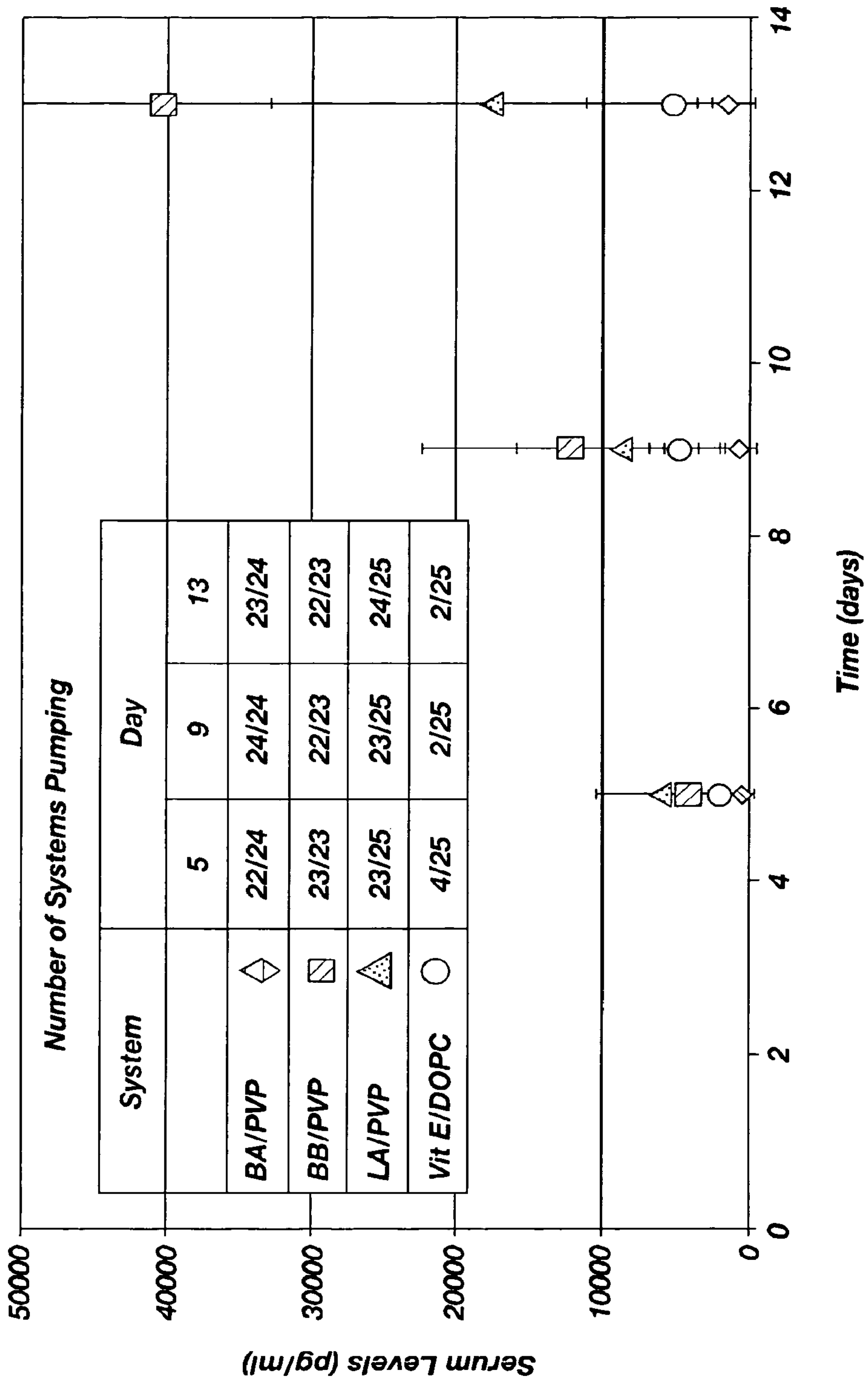
FIG. 9 is a graph illustrating the in vivo release of omega-IFN in rats.
Figure 10:
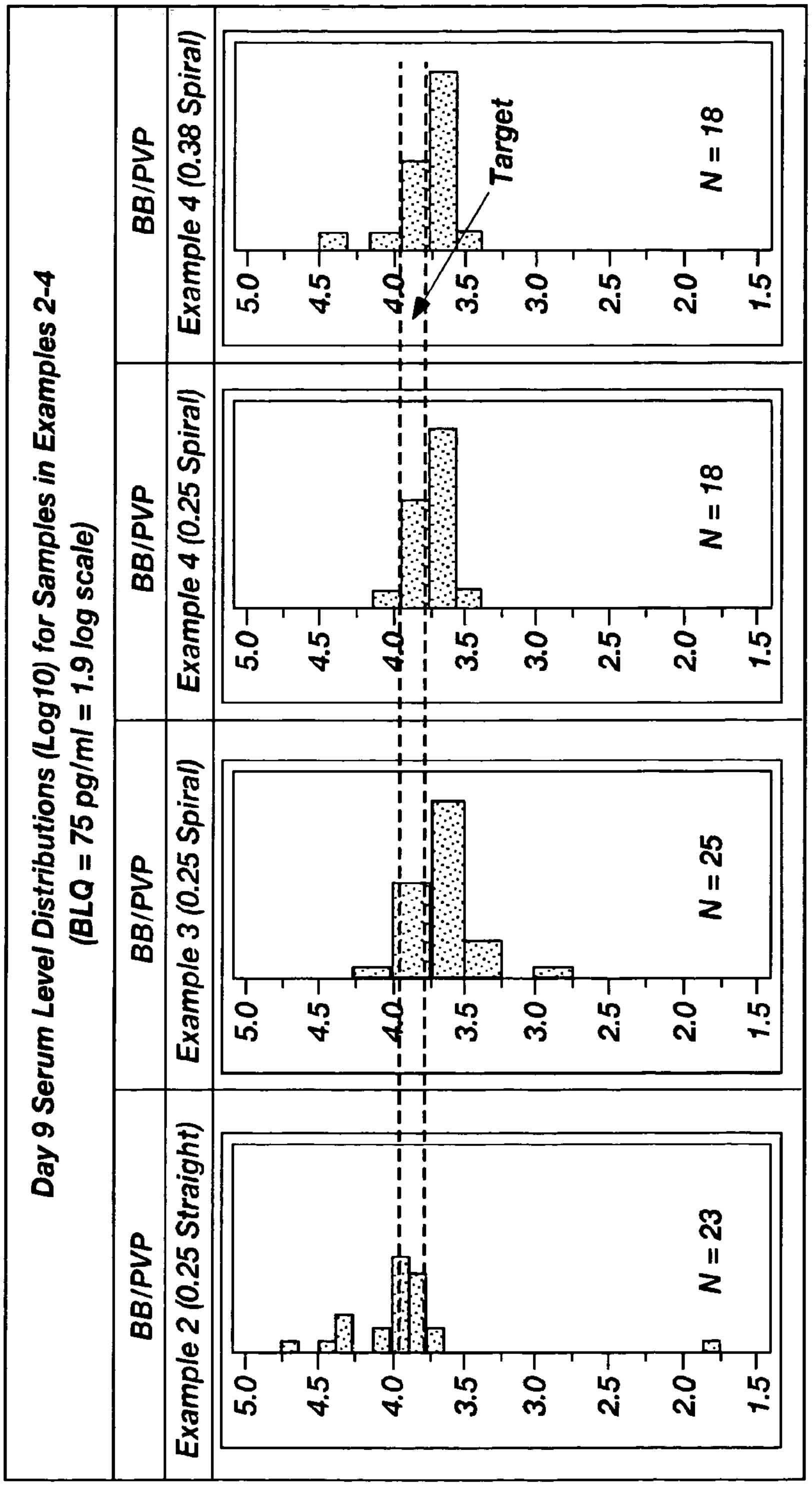
FIG. 10 shows the serum level distributions of omega-IFN nine days after implantation. In the figure, dashed lines represent log of 4000-6000 pg/ml nominal targets.

The in vivo testing of each suspension formulation was conducted by subcutaneously implanting the systems into Fischer rats. Twenty-three systems were implanted unprimed while two systems were primed for approximately seven days prior to implantation. After implantation (t=0), blood samples were drawn and omega-IFN was assayed on day 5, 9, and 13 for each suspension formulation. Protein serum levels at days 5, 9, and 13 after implantation are shown in FIG. 9. Protein serum levels 9 days after implantation are shown in FIG. 10. FIG. 10 further includes protein serum levels of samples described in Examples 3 and 4. As shown in FIG. 10, the serum levels of the omega-IFN are within target ranges. Three systems were explanted at day 45 to assess system integrity. The remaining systems were explanted at day 90, and all systems were intact indicating the implants performed in the planned manner. Twenty rats were required to detect approximately 30% difference. After explantation, systems/animals were tested for membrane expulsion, X-ray for piston position (final explantation only), residual protein assay, macroscopic implantation site evaluation, clinical pathology (excise tissue and selected organs from all animals), implantation site histology at the DM, and assessment of capsule formation at the titanium, polyurethane, and PEEK contacting areas.

Example 3

In Vivo and In Vitro Testing of Suspension Formulations Using a Spiral Diffusion Moderator The suspension formulations described in Example 2 were investigated for system integrity and in vivo release of omega-IFN. This experiment differed from that described in Example 2 in that this experiment was focused on the ability of the suspension formulations to both release measurable omega-IFN in vivo as well as maintain system integrity using a two-piece, spiral PEEK-on-PEEK diffusion moderator with a 0.25 mm diameter and a 15 mm length. The suspension formulations were tested to determine: omega-IFN release in vivo from DUROS® systems after 2, 6, 9, and 13 days of in vivo operation (n=25); failure rates (system integrity) of in vivo systems at 29 days (n=3), 61 days (n=3), and 90 days (n=19) after implantation; the stability of omega-IFN in the suspension formulations over several months at 5° C. and 40° C.; and in vitro release rate pumping into air and aqueous media. The materials used in this experiment are shown in Table 7.

TABLE 7

| Materials Used in the Studies |
|---|
| Omega-IFN |
| Sucrose |
| Methionine |
| Citric Acid Monohydrate |
| Sodium Citrate |
| Povidone 17PF (cleaned) |
| Lauryl Alcohol |
| Benzyl Benzoate |
| Benzyl Alcohol |
| DOPC |
| Vitamin E |
| DUROS ® Implants |
| C-FLEX ® Piston |
| Fluoroelastomer Piston |
| DUROS ® Osmotic Tablet |
| Tecophilic HP-60D-33 |
| DUROS ® Membrane |
| Titanium Reservoir (Gen 3) with colored band |
| Polyethylene Glycol 400 |
| Silicone Fluid, MDM 350 |
| Spiral PEEK-on-PEEK DM (0.25 × 15 mm) |

The suspension vehicles having the compositions shown in Table 8 were prepared as described in Example 2.

TABLE 8

| Summary of Suspension Vehicle Composition (No omega-IFN) | | | | | |
|---|---|---|---|---|---|
| | Solvent | | Structuring Agent | | Nominal |
| Vehicle | Solvent | Composition (% w/w) | Agent | Composition (% w/w) | Viscosity Poise |
| 1 | Benzyl Alcohol (BA) | 39 | PVP | 61 | 15,000 |
| 2 | Benzyl Benzoate (BB) | 49 | PVP | 51 | 15,000 |
| 3 | Lauryl Alcohol (LA) | 45 | PVP | 55 | 15,000 |
| 4 | Vitamin E | 52 | DOPC | 48 | 10,000-60,000 |

The suspension formulations having the compositions shown in Table 9 were prepared as described in Example 2.

TABLE 9

| Target Compositions of Suspension Formulations | | | | | | | | |
|---|---|---|---|---|---|---|---|---|
| | Vehicle Composition (90%) | | | | Drug Particle Composition (10%) | | | |
| Formulation | Solvent | Content (% w/w) | Agent | Content (% w/w) | Sucrose (% w/w) | Methionine (% w/w) | Citrate (% w/w) | ω-INF (% w/w) |
| PDP7-202-1 | BA | 35.1 | PVP | 54.9 | 3.3% | 1.6% | 3.5% | 1.6% |
| PDP7-202-2 | BB | 44.1 | PVP | 45.9 | 3.3% | 1.6% | 3.5% | 1.6% |
| PDP7-202-3 | LA | 40.5 | PVP | 49.5 | 3.3% | 1.6% | 3.5% | 1.6% |
| PDP7-202-4 | Vit. E | 46.8 | DOPC | 43.2 | 3.3% | 1.6% | 3.5% | 1.6% |

The systems were assembled and filled as described in Example 2, except that spiral PEEK-on-PEEK diffusion moderators were used instead of the straight PEEK diffusion moderators of Example 2. Systems were built for in vivo, in vitro, and stability studies, with extra systems built to allow for characterization of the suspension formulation. Microbiological and humidity controls were implemented to minimize bioburden and water content in the product, as described in Table 7 above. A representative number of systems were tested for bioburden and endotoxin to assess possible microbial contamination associated with the finished implant product.

The systems were characterized as indicated in Table 10. A more detailed summary of the stability-sampling plan is provided in Table 11.

TABLE 10

| Characterization Testing of Final Systems | |
|---|---|
| Tests | Sampling quantity and format per formulation |
| In Vivo | 27 Implants |
| Protein Content Assay (serve as stability samples as well as homogeneity samples) | BB/PVP: 24 implants |

TABLE 10-continued

| Characterization Testing of Final Systems | |
|---|---|
| Tests | Sampling quantity and format per formulation |
| Protein Content Assay (serve as stability samples as well as homogeneity samples) | BA/PVP, LA/PVP, VitE/DOPC: 15 implants |
| Bioburden | 3 Implants |
| Endotoxin | 1 Implant |
| X-ray | All |
| Viscosity | 1 ml |
| Density | 2 ml (Extra suspension left in syringe) |
| Density | 10 systems (these systems also used for stability) |
| Moisture of batch | 5 Implants |
| Moisture (stability) | Extra in vivo implants over 25 used for monitoring the moisture of the stability samples over time. |
| In Vitro | BB/PVP: 25 implants |
| In Vitro | BA/PVP, LA/PVP, VitE/DOPC: 15 implants |

TABLE 11

Summary of Stability Samples

| | Sample Number of Implants at Each Storage Condition Sample | | | | | | |
|---|---|---|---|---|---|---|---|
| | 5° C. (Temperature) | | | 40° C. (Temperature) Sample | | | |
| Particles | Time point (months) 3 0.05 g | Time point (months) 6 0.05 g | Time point (months) 12 0 | Time point (months) 1 0.05 g | Time point (months) 2 0 | Time point (months) 3 0.05 g | Time point (months) 6 0 |
| BA/PVP | 3 | 3 | 0 | 3 | 0 | 3 | 0 |
| BB/PVP | 3 | 3 | 3 | 3 | 3 | 3 | 3 |
| LA/PVP | 3 | 3 | 0 | 3 | 0 | 3 | 0 |
| VitE/DOPC | 3 | 3 | 0 | 3 | 0 | 3 | 0 |

Implants used for stability testing were sealed in glass vials under nitrogen. The implants in this experiment contained different batches of the suspension formulations than those described in Example 2, so the stability of omega-IFN in the current suspension batches was also monitored. If available, extra samples were packaged and incorporated into the stability plan to monitor changes in the moisture of the stability samples over time. As a control, samples of protein particles were sealed in glass vials under nitrogen and assayed after 1 and 3 months of storage at 40° C., and after 3 and 6 months of storage at 5° C. Three stability samples were assayed for each time and temperature combination.

The in vivo portion of this study was conducted by subcutaneously implanting the systems into Fischer rats. In all groups, 25 systems were implanted. For the benzyl alcohol/PVP, benzyl benzoate/PVP, and lauryl alcohol/PVP groups, 23 systems were unprimed and 2 systems were primed. For the Vitamin E/DOPC group, 15 systems were unprimed and 10 were primed. The PVP-based systems and the DOPC-based systems were primed for approximately 7 and 5 days, respectively, prior to implantation.

Blood samples were drawn on days 2, 6, 9, and 13 after implantation and the blood was assayed for omega-IFN. Three systems were explanted on day 29 and an additional three systems were explanted on day 61. The remaining systems were explanted on day 90. After explantation, systems/animals were tested for: membrane and piston integrity; piston position (via X-ray); observations of diffusion moderator track and formulation in the drug reservoir; moisture content in the drug reservoir; residual protein content and characteristics (only in systems explanted at day 90); macroscopic implantation site evaluation; clinical pathology (excised tissue and selected organs from all animals); implantation site histology at the diffusion moderator; and assessment of capsule formation at the titanium, polyurethane, and PEEK contacting areas. Protein serum levels 9 days after implantation are shown in FIG. 10. The serum levels of the omega-IFN fell within the target ranges.

The in vitro portion of this study was conducted with approximately two-thirds of the implants delivering the suspension formulation into air and approximately one-third of the implants with the diffusion moderators (DM) immersed in the appropriate aqueous buffer. Aqueous buffers were selected based on a preliminary screening of release rate media performed by Analytical Sciences. Listed in Table 12 are the group size, diffusion moderator, and aqueous medium for each of the suspension formulations. The membrane side of the implant was immersed in phosphate buffered saline at neutral pH containing 0.2% sodium azide. The implants with their diffusion moderators immersed in the aqueous medium were unprimed so that both ends of the implant were hydrated on the same day.

TABLE 12

Release Rate Experimental Plan

| | Diffusion moderators exposed to air | Diffusion moderators exposed to aqueous medium | Aqueous medium on DM side of implant |
|---|---|---|---|
| BA/PVP (Spiral DM) | 8 | 5 | Phosphate buffer, pH 7 |
| BB/PVP (Spiral DM) | 10 | 5 | Citrate buffer, pH 6 |
| BB/PVP (Spiral DM) | 10 | 0 | Citrate buffer, pH 6 |
| LA/PVP (Spiral DM) | 10 | 5 | Phosphate buffer, pH 7 |
| VitE/DOPC (Spiral DM) | 8 | 5 | Citrate buffer, pH 2 |

The systems including the straight diffusion moderators and the benzyl benzoate/PVP suspension formulations were pumped to air only.

Example 4

Effect of Start-up Conditions and Diameter of the Diffusion Moderator on In Vivo and In Vitro Performance The effect of the start-up conditions (primed, unprimed) and diffusion moderator diameter on the behavior of the systems were evaluated in three suspension vehicles (BB/PVP, LA/PVP, and lauryl lactate (LL)/PVP). The experiment used a 2-piece, PEEK-on-PEEK, spiral diffusion moderator with a channel diameter of either 0.25 mm or 0.38 mm. The effect of the diffusion moderator diameter on omega-IFN serum levels and implant survival rates over a 90-day period was determined. The length of the diffusion moderator channel was 35 mm, which is longer than the 15 mm channels used in the experiments described in Examples 2 and 3. The influx of water into the drug reservoir was monitored over time to analyze the required length of the diffusion moderator channel. In addition, the in vitro release of omega-IFN into buffer was studied.

Outputs of the in vivo portion of the study included determining serum levels of omega-IFN on days 2 and 9, at two additional intermediate timepoints, and approximately on days 75-90; failure rates (membrane integrity) of in vivo systems at 13 days (n=2) and 90 days (n=7) after implantation; and water influx into the drug reservoir of the implant at 13 days (n=2) and 90 days (n=7) after implantation. The groups used in the in vivo portion of the study are shown in Table 13.

TABLE 13

Description of the Groups Planned for the In Vivo portion of the Study Description

| Group | Formulation | DM Inner Diameter | DM Channel Length | Priming | Total N/group |
|---|---|---|---|---|---|
| 1 | BB/PVP | 0.25 mm | 35 mm (2 piece) | Yes | 9 |
| 2 | BB/PVP | 0.25 mm | 35 mm (2 piece) | No | 9 |
| 3 | BB/PVP | 0.38 mm | 35 mm (2 piece) | Yes | 9 |
| 4 | BB/PVP | 0.38 mm | 35 mm (2 piece) | No | 9 |
| 5 | LA/PVP | 0.25 mm | 35 mm (2 piece) | Yes | 9 |
| 6 | LA/PVP | 0.25 mm | 35 mm (2 piece) | No | 9 |
| 7 | LA/PVP | 0.38 mm | 35 mm (2 piece) | Yes | 9 |
| 8 | LA/PVP | 0.38 mm | 35 mm (2 piece) | No | 9 |
| 9 | LL/PVP | 0.25 mm | 35 mm (2 piece) | Yes | 9 |
| 10 | LL/PVP | 0.25 mm | 35 mm (2 piece) | No | 9 |
| 11 | LL/PVP | 0.38 mm | 35 mm (2 piece) | Yes | 9 |
| 12 | LL/PVP | 0.38 mm | 35 mm (2 piece) | No | 9 |

The materials used in this experiment are shown in Table 14.

TABLE 14

| Materials Used in the Studies |
|---|
| Drug Particles |
| Omega-IFN |
| Sucrose |
| Methionine |
| Citric Acid Monohydrate |
| Sodium Citrate |
| Povidone 17PF (cleaned) |
| Lauryl Alcohol (Spectrum Chemical) |
| Benzyl Benzoate (Tessenderlo) |
| Lauryl Lactate (Chemic Laboratories) |
| DUROS ® Implants |
| C-FLEX ® Piston |
| Fluoroelastomer Piston |
| Hydrosil Coating |
| DUROS ® Osmotic Tablet |
| Tecophilic HP-60D-33 |
| DUROS ® Membrane (clear) |
| Titanium Reservoir (Gen 3) with colored band |
| Polyethylene Glycol 400 |
| Silicone Fluid, MDM 350 |

TABLE 14-continued

| Materials Used in the Studies |
|---|
| Spiral PEEK-on-PEEK DM (0.25 × 35 mm) |
| Spiral PEEK-on-PEEK DM (0.38 × 35 mm) |
| Spiral PEEK-on-PEEK DM (0.25 × 15 mm) |

The formulations of the omega-IFN suspended in various vehicles were tested for stability, in vivo release, and in vitro release. The omega-IFN was prepared as described in Example 2. This study used 150 microliter Gen 3 titanium reservoirs with color band fitted with clear Tecophilic HP-60D-33 membranes annealed for 7 days at 65° C. in a low humidity forced air oven. Three suspension vehicles were prepared and tested: benzyl benzoate/PVP, lauryl alcohol/PVP, and lauryl lactate/PVP. A summary of the suspension vehicle compositions is presented in Table 15.

TABLE 15

Suspension Vehicle Compositions

| | Solvent | | Viscosity Enhancer | |
|---|---|---|---|---|
| Vehicle | Solvent | Composition (% w/w) | Agent | Composition (% w/w) |
| 1 | Benzyl Benzoate | 49 | PVP | 51 |
| 2 | Lauryl Alcohol | 45 | PVP | 55 |
| 3 | Lauryl Lactate | 50 | PVP | 50 |

The suspension vehicles were prepared in 60 g lots. To minimize residual moisture levels in the polymeric based formulations, lyophilized PVP was used. The methionine and moisture content were measured in the lyophilized PVP before preparing the suspension vehicles. The suspension vehicles were prepared using the Lightnin Overhead Mixer fitted with a spatula blade for the stirring paddle and then visually inspected for particulates before proceeding. If necessary, the suspension vehicle was centrifuged at 4,000 rpm at 65° C. for 1 hour to remove any particles. The viscosity of the suspension vehicles was measured.

Target compositions of the suspension formulations are shown in Table 16.

TABLE 16

Target Compositions of Suspension Formulations.

| | Vehicle Composition (90%) | | | | Drug Particle Composition (10%) | | | |
|---|---|---|---|---|---|---|---|---|
| Formulation | Solvent | Content (% w/w) | Agent | Content (% w/w) | Sucrose (% w/w) | Methionine (% w/w) | Citrate (% w/w) | ω-INF (% w/w) |
| PDP7-203-1 | BB | 44.1 | PVP | 45.9 | 3.3% | 1.6% | 3.5% | 1.6% |
| PDP7-203-2 | LA | 40.5 | PVP | 49.5 | 3.3% | 1.6% | 3.5% | 1.6% |
| PDP7-203-3 | LL | 45.0 | PVP | 45.0 | 3.3% | 1.6% | 3.5% | 1.6% |

Each suspension formulation had a target particle loading of approximately 10% (w/w). The omega-IFN was incorporated into the suspension vehicle by hand using a metal spatula with the suspension vehicle warmed on a hotplate.

The suspension formulations were filled in 10 mL syringes, deaerated under vacuum, and sealed in polyfoil pouches. The syringes were stored at room temperature in a drybox until filling into subassemblies.

The subassemblies and diffusion moderators were prepared as described in Example 3. To insert the diffusion moderators for the LL/PVP suspension formulations, the systems were placed into labeled vials membrane side down and stoppered but not crimped. The systems were removed from the drybox and fitted with spiral PEEK-on-PEEK diffusion moderators with channel dimensions of either 0.25 mm×35 mm or 0.38 mm×35 mm. The vials were opened just prior to insertion of the diffusion moderators. The vials were then restoppered and brought back into the drybox in batches to ensure that the exposure time outside the drybox did not exceed 30 minutes. Each system was equilibrated 30 minutes in the drybox in unstoppered vials before being restoppered and crimped.

To insert the diffusion moderators for the BB/PVP and LA/PVP suspension formulations, the filled systems were placed back into the subassembly trays. After the lid was put back in place, the subassembly trays were sealed in two layers of polyfoil bags and left in the drybox until shortly before use. Packages of the subassembly trays were opened under nitrogen atmosphere inside of the isolator. Trays containing DM/DM guide assemblies were placed in tray heaters and allowed to equilibrate for at least 30 minutes prior to insertion. Diffusion moderators with 0.25 mm diameter channels were heated to 75° C. Diffusion moderators with 0.38 mm diameter channels were heated to 65° C. Each filled subassembly was cleaned on the outside with a sterile wipe, if needed, and seated in the DM insertion nest. After the nest was pressurized, a DM guide assembly was placed over the end of the subassembly and the DM inserter was immediately activated. Diffusion moderator insertion was carried out at approximately 3 mm/minute. After DM insertion, the system was allowed to sit in the nest for approximately 15 seconds and the end of the system was wiped with a sterile wipe. Systems were transferred from the nest to vials. After finishing a rack of 24 vials, vials were stoppered and crimp sealed in the isolator.

The final systems were characterized as indicated in Table 17.

TABLE 17

Characterization Testing of Final Systems

| Tests | Sampling quantity and format per formulation |
|---|---|
| In Vivo | 40 Implants |
| Protein Stability (also served as homogeneity samples) | BB/PVP: 9 implants |
| Protein Stability (also served as homogeneity samples) | LA/PVP: 21 implants |
| Protein Stability (also served as homogeneity samples) | LL/PVP: 21 implants |
| Bioburden | 3 Implants |
| Endotoxin | 1 Implant |
| X-ray | All |
| N-Ray | 24 implants (in vitro systems) |
| Viscosity | 1 ml (If extra suspension remains in the syringes) |
| Density | 2 ml (If extra suspension remains in the syringes) |
| Moisture of batch at t = 0 | 4 implants |
| Moisture | Extra systems will be used for monitoring the moisture of the implants over time. |
| In Vitro | BB/PVP: 24 implants |
| In Vitro | LA/PVP: 30 implants |
| In Vitro | LL/PVP: 24 implants |

A more detailed summary of the stability-sampling plan is given in Table 18.

TABLE 18

Summary of Stability Samples

| | Sample Number of Implants at Each Storage Condition (in addition to t = 0) Sample | | | | | | |
|---|---|---|---|---|---|---|---|
| | 5° C. (Temperature) | | | 40° C. (Temperature) Sample | | | |
| Particles | Time point (months) 3 0 | Time point (months) 6 0 | Time point (months) 12 0 | Time point (months) 1 0.05 g | Time point (months) 2 0 | Time point (months) 3 0.05 g | Time point (months) 6 0 |
| BB/PVP | 0 | 0 | 0 | 3 | 0 | 3 | 0 |
| LA/PVP | 0 | 3 | 3 | 3 | 3 | 3 | 3 |
| LL/PVP | 0 | 3 | 3 | 3 | 3 | 3 | 3 |

Implants used for stability testing were sealed in glass vials under nitrogen. The stability of the omega-IFN in the BB/PVP suspension vehicle was tested in previous experiments; therefore, a smaller stability schedule was tested in the current experiment. A larger stability study was conducted for the LA/PVP and the LL/PVP suspension formulations since new sources of solvents were used in the present study. If available, extra samples were packaged and incorporated into the stability plan to monitor changes in the moisture of the stability samples over time. As a control, samples of protein particles were sealed in glass vials under nitrogen and assayed at t=0 and after 1 and 3 months of storage at 40° C. Three stability samples were assayed for each time and temperature combination planned.

The in vivo portion of this study was conducted by subcutaneously implanting the systems into Fischer rats. In each of the 12 groups outlined in Table 19, nine systems were implanted. In the groups that were primed, the length of priming was 4-5 days.

TABLE 19

| Description of Groups Planned for the In Vivo Portion of the Study Description | | | | | |
|---|---|---|---|---|---|
| Group | Formulation | DM Inner Diameter | DM Channel Length | Priming | Total N/group |
| 1 | BB/PVP | 0.25 mm | 35 mm (2 piece) | Yes | 9 |
| 2 | BB/PVP | 0.25 mm | 35 mm (2 piece) | No | 9 |
| 3 | BB/PVP | 0.38 mm | 35 mm (2 piece) | Yes | 9 |
| 4 | BB/PVP | 0.38 mm | 35 mm (2 piece) | No | 9 |
| 5 | LA/PVP | 0.25 mm | 35 mm (2 piece) | Yes | 9 |
| 6 | LA/PVP | 0.25 mm | 35 mm (2 piece) | No | 9 |
| 7 | LA/PVP | 0.38 mm | 35 mm (2 piece) | Yes | 9 |
| 8 | LA/PVP | 0.38 mm | 35 mm (2 piece) | No | 9 |
| 9 | LL/PVP | 0.25 mm | 35 mm (2 piece) | Yes | 9 |
| 10 | LL/PVP | 0.25 mm | 35 mm (2 piece) | No | 9 |
| 11 | LL/PVP | 0.38 mm | 35 mm (2 piece) | Yes | 9 |
| 12 | LL/PVP | 0.38 mm | 35 mm (2 piece) | No | 9 |

Blood samples were drawn on days 2 and 9 after implantation, and the blood was assayed for omega-IFN. Two systems were explanted on day 13 and the remaining systems were explanted at day 90. After explantation, systems/animals were tested for membrane and piston integrity, X-ray for piston position, observations of DM track and formulation in the drug reservoir, moisture content in the drug reservoir, residual protein content and characteristics (only in systems explanted at day 90), macroscopic implantation site evaluation, clinical pathology (excise tissue and selected organs from all animals), implantation site histology at the DM, and assessment of capsule formation at the titanium, polyurethane, and PEEK contacting areas. Protein serum levels that were measured 9 days after implantation are shown in FIG. 10. The serum levels of the omega-IFN fell within the target ranges.

In the in vitro portion of this experiment, half of the implants were primed and the remaining half of the implants had the diffusion moderator and membrane immersed in aqueous buffer on the same day (unprimed). The release rate medium was determined to be an appropriate aqueous buffer. Listed in Table 20 are the group size, diffusion moderator, and start-up conditions for each of the suspension formulations.

TABLE 20

| Description of Groups Planned for the In Vitro Portion of the Study Description | | | | | |
|---|---|---|---|---|---|
| Group | Formulation | DM Inner Diameter | DM Channel Length | Start-up conditions | Total N/group |
| 1 | BB/PVP | 0.25 mm | 35 mm (2 piece) | Primed | 6 |
| 2 | BB/PVP | 0.25 mm | 35 mm (2 piece) | Unprimed | 6 |
| 3 | BB/PVP | 0.38 mm | 35 mm (2 piece) | Primed | 6 |
| 4 | BB/PVP | 0.38 mm | 35 mm (2 piece) | Unprimed | 6 |
| 5 | LA/PVP | 0.25 mm | 35 mm (2 piece) | Primed | 6 |
| 6 | LA/PVP | 0.25 mm | 35 mm (2 piece) | Unprimed | 6 |
| 7 | LA/PVP | 0.38 mm | 35 mm (2 piece) | Primed | 6 |
| 8 | LA/PVP | 0.38 mm | 35 mm (2 piece) | Unprimed | 6 |
| 9 | LL/PVP | 0.25 mm | 35 mm (2 piece) | Primed | 6 |
| 10 | LL/PVP | 0.25 mm | 35 mm (2 piece) | Unprimed | 6 |
| 11 | LL/PVP | 0.38 mm | 35 mm (2 piece) | Primed | 6 |
| 12 | LL/PVP | 0.38 mm | 35 mm (2 piece) | Unprimed | 6 |
| 13 | LA/PVP | 0.25 mm | 15 mm (2 piece) | Primed | 6 |

The membrane side of the implant was immersed in phosphate buffered saline at neutral pH containing 0.2% sodium azide. Group 13 was included as a control group.

The 72 systems in groups 1 through 12 were sent for N-ray imaging prior to testing in vitro to provide a greater level of detail about the systems than can be provided by X-ray due to the superior resolution of the contents of the implant when N-ray is performed.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A stable, nonaqueous suspension formulation, comprising:

a particle formulation comprising an active agent and an excipient, wherein the active agent comprises a peptide, polypeptide, or protein, and the excipient comprises methionine; and a nonaqueous, single-phase vehicle consisting essentially of about 10% to about 90% (w/w) polyvinylpyrrolidone and about 90% to about 10% (w/w) benzyl benzoate, wherein the vehicle has a viscosity of between approximately 10,000 poise to approximately 20,000 poise measured at 37° C.

2. The suspension formulation of claim 1, wherein the particle formulation comprises one or more additional excipients.

3. The suspension formulation of claim 2, wherein the one or more additional excipients are selected from the group consisting of citrate buffer, sucrose, succinate, and dextran.

4. The suspension formulation of claim 2, wherein the one or more additional excipients comprise sucrose and citrate buffer.

5. The suspension formulation of claim 1, wherein the single-phase vehicle consists essentially of about 25% to about 75% (w/w) polyvinylpyrrolidone and about 75% to about 25% (w/w) benzyl benzoate.

6. The suspension formulation of claim 1, wherein the particle formulation is formed by lyophilization, spray-drying, or freeze-drying.

7. The suspension formulation of claim 1, wherein the particle formulation is present in the suspension formulation in a range from approximately 0.1 to 50 wt %.

8. The suspension formulation of claim 1, wherein the particle formulation is present in the suspension formulation in a range from approximately 3 to 12 wt %.

9. A method of making the suspension formulation of claim 1, the method comprising blending the polyvinylpyrrolidone and benzyl benzoate to form the single-phase vehicle, wherein a vacuum is applied during blending to remove air bubbles; and adding the particle formulation to form the suspension formulation.

10. The method of claim 9, wherein the vacuum is between about −5 to about −10 Hg.

11. The method of claim 10, further comprising increasing the vacuum after the polyvinylpyrrolidone is incorporated into the benzyl benzoate to about −30 Hg.

* * * * *

UNITED STATES PATENT AND TRADEMARK OFFICE

CERTIFICATE OF CORRECTION

PATENT NO. : 8,440,226 B2
APPLICATION NO. : 13/526375
DATED : May 14, 2013
INVENTOR(S) : Catherine M. Rohloff et al.

It is certified that error appears in the above-identified patent and that said Letters Patent is hereby corrected as shown below:

In the Specification

In col. 4, line 11, delete “alcohol, an d PVP”, and insert -- alcohol, and PVP --, therefor.

In col. 4, line 20, delete “(i) benzyl-time;”, and insert -- (i) benzyl benzoate and PVP and (ii) benzyl benzoate, benzyl alcohol, and PVP at 40° C. as a function of time; --, therefor.

In cols. 15-16, lines 1-20, delete

TABLE 6

“

| Summary of Stability Samples | | | | | | | |
|---|---|---|---|---|---|---|---|
| | Sample<br>Number of Samples<br>Sample | | | | | | |
| | 5° C. (Temperature) | | | 40° C. (Temperature) | | | |
| | Sample | | | | | | |
| Particles | Time point (months) 3 0.05 g | Time point (months) 6 0.05 g | Time point (months) 12 0.05 g | Time point (months) 1 0.05 g | Time point (months) 2 0.05 g | Time point (months) 3 0.05 g | Time point (months) 6 0.05 g |
| 1 | 3 sys. | 3 sys. | 3 sys. | 3 sys. | 3 sys. | 3 sys. | 3 sys. |
| 2 | 3 sys. | 3 sys. | 3 sys. | 3 sys. | 3 sys. | 3 sys. | 3 sys. |
| 3 | 3 sys. | 3 sys. | 3 sys. | 3 sys. | 3 sys. | 3 sys. | 3 sys. |
| 4 | 3 sys. | 3 sys. | 3 sys. | 3 sys. | 3 sys. | 3 sys. | 3 sys. |

” 32

(continued next page)

and insert

Signed and Sealed this
Second Day of July, 2013

Teresa Stanek Rea
*Acting Director of the United States Patent and Trademark Office*

Table 6: Summary of Stability Samples

| Sample | Number of Samples | | | | | | |
|---|---|---|---|---|---|---|---|
| Sample | 5°C (Temperature) | | | 40°C (Temperature) | | | |
| Sample | Time point (months) 3 | Time point (months) 6 | Time point (months) 12 | Time point (months) 1 | Time point (months) 2 | Time point (months) 3 | Time point (months) 6 |
| Particles | 0.05 g | 0.05 g | 0.05 g | 0.05 g | 0.05 g | 0.05 g | 0.05 g |
| 1 | 3 sys. | 3 sys. | 3 sys. | 3 sys. | 3 sys. | 3 sys. | 3 sys. |
| 2 | 3 sys. | 3 sys. | 3 sys. | 3 sys. | 3 sys. | 3 sys. | 3 sys. |
| 3 | 3 sys. | 3 sys. | 3 sys. | 3 sys. | 3 sys. | 3 sys. | 3 sys. |
| 4 | 3 sys. | 3 sys. | 3 sys. | 3 sys. | 3 sys. | 3 sys. | 3 sys. |

-- --, therefor.

In cols. 17-18, lines 1-15, delete

TABLE 8

Summary of Suspension Vehicle Composition (No omega-IFN)

| Vehicle | Solvent (Solvent) | Solvent Composition (% w/w) | Structuring Agent (Agent) | Structuring Agent Composition (% w/w) | Nominal Viscosity Poise |
|---|---|---|---|---|---|
| 1 | Benzyl Alcohol (BA) | 39 | PVP | 61 | 15,000 |
| 2 | Benzyl Benzoate (BB) | 49 | PVP | 51 | 15,000 |
| 3 | Lauryl Alcohol (LA) | 45 | PVP | 55 | 15,000 |
| 4 | Vitamin E | 52 | DOPC | 48 | 10,000-60,000 |

" "

and insert

Table 8: Summary of Suspension Vehicle Composition (No omega-IFN)

| Vehicle | Solvent | | Structuring Agent | | Nominal Viscosity |
|---|---|---|---|---|---|
| | Solvent | Composition (%w/w) | Agent | Composition (%w/w) | Poise |
| 1 | Benzyl Alcohol (BA) | 39 | PVP | 61 | 15,000 |
| 2 | Benzyl Benzoate (BB) | 49 | PVP | 51 | 15,000 |
| 3 | Lauryl Alcohol (LA) | 45 | PVP | 55 | 15,000 |
| 4 | Vitamin E | 52 | DOPC | 48 | 10,000-60,000 |

-- --, therefor.

In cols. 19-20, lines 1-18, delete

TABLE 11

| Summary of Stability Samples | | | | | | | |
|---|---|---|---|---|---|---|---|
| | Sample<br>Number of Implants at Each Storage Condition<br>Sample | | | | | | |
| | 5° C. (Temperature) | | | 40° C. (Temperature) | | | |
| | Sample | | | | | | |
| Particles | Time point (months) 3<br>0.05 g | Time point (months) 6<br>0.05 g | Time point (months) 12<br>0 | Time point (months) 1<br>0.05 g | Time point (months) 2<br>0 | Time point (months) 3<br>0.05 g | Time point (months) 6<br>0 |
| BA/PVP | 3 | 3 | 0 | 3 | 0 | 3 | 0 |
| BB/PVP | 3 | 3 | 3 | 3 | 3 | 3 | 3 |
| LA/PVP | 3 | 3 | 0 | 3 | 0 | 3 | 0 |
| VitE/DOPC | 3 | 3 | 0 | 3 | 0 | 3 | 0 |

and insert

Table 11: Summary of Stability Samples

| Sample | Number of Implants at Each Storage Condition | | | | | | |
|---|---|---|---|---|---|---|---|
| Sample | 5°C (Temperature) | | | 40°C (Temperature) | | | |
| Sample | Time point (months) 3 | Time point (months) 6 | Time point (months) 12 | Time point (months) 1 | Time point (months) 2 | Time point (months) 3 | Time point (months) 6 |
| Particles | 0.05 g | 0.05 g | 0 | 0.05 g | 0 | 0.05 g | 0 |
| BA/PVP | 3 | 3 | 0 | 3 | 0 | 3 | 0 |
| BB/PVP | 3 | 3 | 3 | 3 | 3 | 3 | 3 |
| LA/PVP | 3 | 3 | 0 | 3 | 0 | 3 | 0 |
| VitE/DOPC | 3 | 3 | 0 | 3 | 0 | 3 | 0 |

therefor.

In col. 22, line 55 (i.e., Table 16, line 4) delete "ω-INF", and insert -- ω-IFN --, therefor.

In cols. 23-24 lines 33-50, delete

TABLE 18

Summary of Stability Samples

| Particles | Time point (months) 3 | Time point (months) 6 | Time point (months) 12 | Time point (months) 1 | Time point (months) 2 | Time point (months) 3 | Time point (months) 6 |
|---|---|---|---|---|---|---|---|
| | Sample Number of Implants at Each Storage Condition (in addition to t = 0) Sample | | | | | | |
| | 5° C. (Temperature) | | | 40° C. (Temperature) | | | |
| | Sample | | | | | | |
| | 0 | 0 | 0 | 0.05 g | 0 | 0.05 g | 0 |
| BB/PVP | 0 | 0 | 0 | 3 | 0 | 3 | 0 |
| LA/PVP | 0 | 3 | 3 | 3 | 3 | 3 | 3 |
| LL/PVP | 0 | 3 | 3 | 3 | 3 | 3 | 3 |

" "

and insert

Table 18: Summary of Stability Samples

| Sample | Number of Implants at Each Storage Condition (in addition to t = 0) | | | | | | |
|---|---|---|---|---|---|---|---|
| Sample | 5°C (Temperature) | | | 40°C (Temperature) | | | |
| Sample | Time point (months) 3 | Time point (months) 6 | Time point (months) 12 | Time point (months) 1 | Time point (months) 2 | Time point (months) 3 | Time point (months) 6 |
| Particles | 0 | 0 | 0 | 0.05 g | 0 | 0.05 g | 0 |
| BB/PVP | 0 | 0 | 0 | 3 | 0 | 3 | 0 |
| LA/PVP | 0 | 3 | 3 | 3 | 3 | 3 | 3 |
| LL/PVP | 0 | 3 | 3 | 3 | 3 | 3 | 3 |

-- --, therefor.